(12) United States Patent
Dothie

(10) Patent No.: US 9,283,560 B2
(45) Date of Patent: Mar. 15, 2016

(54) PASSIVE MICROFLUIDIC METERING DEVICE

(71) Applicant: SHARP KABUSHIKI KAISHA, Osaka (JP)

(72) Inventor: Pamela Ann Dothie, Chilton (GB)

(73) Assignee: Sharp Kabushiki Kaisha, Osaka (JP)

( * ) Notice: Subject to any disclaimer, the term of this patent is extended or adjusted under 35 U.S.C. 154(b) by 175 days.

(21) Appl. No.: 14/087,506

(22) Filed: Nov. 22, 2013

(65) Prior Publication Data

US 2015/0147777 A1    May 28, 2015

(51) Int. Cl.
*B01L 3/00* (2006.01)
*G01N 15/14* (2006.01)

(52) U.S. Cl.
CPC ....... *B01L 3/502715* (2013.01); *B01L 3/50273* (2013.01); *B01L 3/502723* (2013.01); *B01L 3/502738* (2013.01); *G01N 15/1404* (2013.01); *B01L 2200/0605* (2013.01); *B01L 2200/0626* (2013.01); *B01L 2300/0627* (2013.01); *B01L 2300/087* (2013.01); *B01L 2300/0867* (2013.01); *B01L 2400/0478* (2013.01); *B01L 2400/0487* (2013.01); *B01L 2400/0622* (2013.01); *B01L 2400/0683* (2013.01); *B01L 2400/0694* (2013.01); *B01L 2400/086* (2013.01); *Y10T 436/2575* (2015.01)

(58) Field of Classification Search
CPC .......... B01L 3/502715; B01L 3/50273; B01L 3/502723; B01L 3/502738; B01L 2200/0605; B01L 2200/0626; B01L 2300/0867; B01L 2300/087; B01L 2300/0627; B01L 2400/0478; B01L 2400/04; G01N 15/1404
See application file for complete search history.

(56) References Cited

U.S. PATENT DOCUMENTS

| 4,761,381 | A | * | 8/1988 | Blatt et al. ................... 436/165 |
| 5,208,163 | A |  | 5/1993 | Charlton et al. |
| 6,656,428 | B1 | * | 12/2003 | Clark et al. ................... 422/404 |
| 2002/0042125 | A1 | * | 4/2002 | Petersen et al. ............ 435/287.2 |
| 2003/0083685 | A1 | * | 5/2003 | Freeman et al. .............. 606/181 |

(Continued)

FOREIGN PATENT DOCUMENTS

| EP | 0392851 B1 | 10/1990 |
| WO | WO 2011/087813 A2 | 7/2011 |

OTHER PUBLICATIONS

European Search Report for corresponding European application No. 14194264.9 dated Apr. 28, 2015.

*Primary Examiner* — Lyle Alexander
*Assistant Examiner* — Jennifer Wecker
(74) *Attorney, Agent, or Firm* — Renner, Otto, Boisselle & Sklar, LLP

(57) ABSTRACT

An integrated fluidic device comprising includes an input chamber that provides an input of a sample fluid, and a first overspill chamber in fluid communication with the input chamber. A metering conduit is in fluid communication with the fluid input chamber and the first overspill chamber. The metering conduit meters a first metered volume of fluid from the sample fluid, and the first overspill chamber receives fluid in excess of the first metered volume of fluid. A second overspill chamber is in fluid communication with the metering conduit. The metering conduit meters a second metered volume of fluid from the first metered volume of fluid, and the second overspill chamber receives fluid from the first metered volume of fluid in excess of the second metered volume of fluid. The second overspill chamber has a fluid actuated closable valve for controlling the metering of the second metered volume of fluid.

13 Claims, 32 Drawing Sheets

(56) References Cited

U.S. PATENT DOCUMENTS

| | | | |
|---|---|---|---|
| 2006/0013725 A1* | 1/2006 | Larsen | 422/57 |
| 2007/0166200 A1* | 7/2007 | Zhou et al. | 422/100 |
| 2008/0108122 A1* | 5/2008 | Paul et al. | 435/183 |
| 2010/0230613 A1* | 9/2010 | Pieprzyk et al. | 250/459.1 |
| 2010/0291588 A1* | 11/2010 | McDevitt et al. | 435/7.2 |
| 2012/0142020 A1 | 6/2012 | Miller | |
| 2012/0171662 A1* | 7/2012 | Broyer et al. | 435/5 |
| 2013/0112296 A1* | 5/2013 | Lee et al. | 137/559 |

* cited by examiner

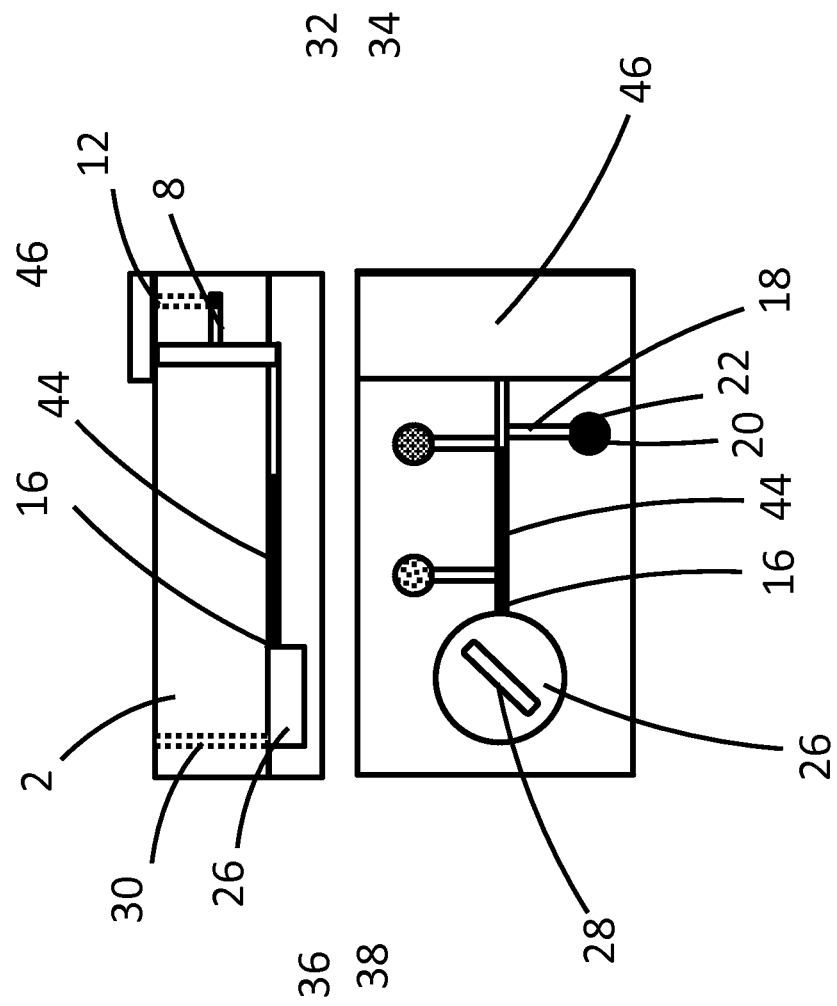

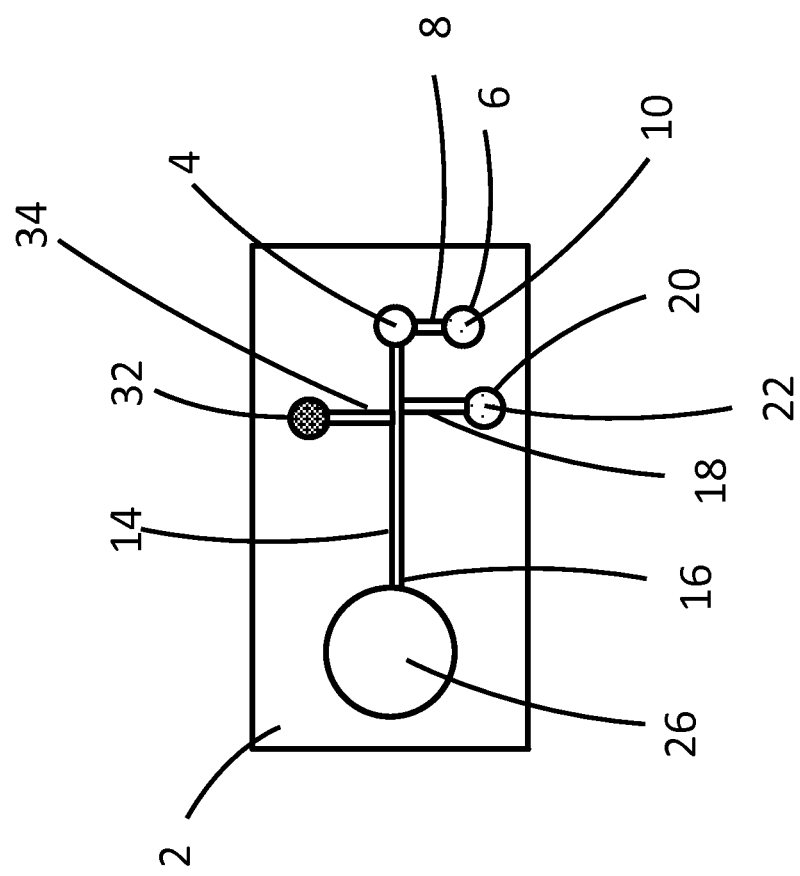

PASSIVE MICROFLUIDIC METERING DEVICE

TECHNICAL FIELD

This invention relates to apparatuses for passively metering a volume of fluid, and more particularly to a microfluidic device that meters successive volumes of fluid for performing a series of fluidic operations.

BACKGROUND ART

The known art describes microfluidic metering apparatuses that meter a single volume of fluid from an input volume of fluid. The known art is limited in operational functionality as it requires an additional, often mechanical, means to meter off a small volume of fluid, such as by using air pressure to force a known volume of liquid away from a larger volume of liquid. The prior art also does not adequately isolate the input volume of fluid from the metered fluid, which increases the possibility of contamination and inaccurate metering.

Patent Blatt et al. U.S. Pat. No. 4,761,381 (issued Feb. 26, 1987) discloses a device where, once a reaction chamber is filled via capillary action, excess fluid will flow through another capillary channel into an overflow chamber. The chambers are configured to try to prevent fluid flowing from the overflow channel back into the reaction chamber. Excess fluid in the overflow chamber is not held securely within the overflow chamber and could either leak out of the vent hole in the chamber, thus contaminating the device, or leak back into the reaction chamber if the device is moved during operation. Furthermore, Blatt et al. does not disclose the ability to passively meter a second volume of fluid from a passively metered first volume of fluid.

Patent Charlton et al. U.S. Pat. No. 5,208,163 (issued Dec. 6, 1991) discloses a method of self-metering fluid within an analysis device. A sample is introduced into the device via an entry port, which fills a metering chamber and access hole. A filter acts as a wick to draw blood into a reaction chamber, which comprises an absorbent membrane. Once the absorbent membrane is saturated, excess fluid is drawn down a metering capillary channel. The metered volume of fluid in this device is absorbed into an absorbent membrane and thus is not in free liquid form. Charlton et al. does not disclose the ability to accurately passively meter a first volume of fluid, and then passively meter a second volume of fluid from the first volume of fluid, where the second volume of metered fluid is maintained in a liquid form. Furthermore, Charlton et al. does not adequately prevent any excess fluid from re-entering the reaction chamber if the device is moved.

Patent Besemer et al. EP0392851B1 (issued Oct. 17, 1990) discloses a dilution and mixing cartridge that uses capillary flows and gravity to control the flow of fluid into a cartridge. Input fluid flows vertically down an input channel into a metering channel. Excess fluid then drains into an overflow channel. However, the device can only be operated in an upright position. Besemer et al. does not disclose the ability to passively meter a second volume of fluid from a passively metered first volume of fluid.

Patent Miller US 2012/0142020A1 (issued Dec. 1, 2011) discloses a sample metering and assay device with integrated sample dilution. A liquid sample is introduced through a sample entry port and capillary, which fills an input channel up to a capillary stop. The input port is sealed, and a second fluid is injected at a specific point along the input channel which meters off a small portion of the input sample. Miller does not disclose the ability to passively meter a second volume of fluid from a passively metered first volume of fluid.

While the known art discloses the use of capillary flows to meter a defined volume of fluid from an input volume of fluid, the art does not disclose the ability to sequentially passively meter a first defined volume of fluid from an input fluid, and then passively meter a second volume of fluid from the first metered volume of fluid, wherein all the excess fluid, in both metering steps, is absorbed by absorbent material leaving a defined volume of fluid in a fluidic channel. Thus, the prior art is limited in terms of both its accuracy, and its ability to further manipulate the second metered volume of fluid.

SUMMARY OF INVENTION

There exists a need in the art for a microfluidic device that can cope with a variety of sample input volumes, by passively metering a first known volume of fluid, and then passively metering an accurate, defined second volume of fluid on which additional fluidic operations can be performed. Furthermore, there exists a need in the art for a device that can cope with a range of fluid input volumes, sequentially meter a first and second volume of fluid, and ensure that all excess fluid is absorbed by an absorbent material so that accidental contamination of the metered sample, and/or the device housing, is prevented.

The disclosed invention has the ability to cope with a range of sample input volumes, by performing a first passive metering operation, with excess fluid from the first fluidic metering step absorbed by an absorbent material. A second volume of fluid is then passively metered from the first volume of fluid, with excess fluid from the second metering step absorbed by an absorbent material. Further fluidic operations can then be performed on the second passively metered volume of fluid. Fluidic operations that may be performed on the second passively metered volume of fluid include lysing, quenching, diluting, labeling, mixing, and others known in the art.

In exemplary embodiments, a microfluidic device accurately and passively meters a first volume of fluid from a sample input volume, and then passively meters a second volume of fluid from the first metered volume of fluid. A series of fluidic operations can then be carried out on the second volume of metered fluid. Excess fluid is absorbed by absorbent material in a first overspill chamber in the first metering operation, and an absorbent material in a second overspill chamber in the second metering operation.

Specifically, the microfluidic device accurately and passively meters a small volume of fluid in a microfluidic metering conduit contained within a housing. The housing contains a plurality of fluidic conduits in communication with the metering conduit and a mixing chamber, enabling fluidic operations to be performed on the second metered volume of fluid. Fluidic operations can be performed on the second metered volume of fluid via the fluidic conduits and the mixing chamber. Excess sample input fluid is absorbed by absorbent materials, preventing any potential hazardous waste leaking from the device.

An aspect of the invention is an integrated fluidic device for passively metering two volumes of fluid in succession. In exemplary embodiments, the integrated fluidic device includes:

A housing;
A fluid input chamber;
A first overspill conduit, in communication with the fluid input chamber;

A first overspill chamber, in communication with the first overspill conduit, containing a first absorbent pad and a first vent hole;

A metering conduit in communication with the fluid input chamber;

A second overspill conduit, in communication with the metering conduit;

A second overspill chamber, in communication with the second overspill conduit, containing a second absorbent pad and fluid actuated closable valve;

A capillary stop in communication with the end of the metering conduit;

A mixing chamber in communication with the capillary stop;

At least one further fluid input conduit in communication with the metering conduit;

A fluid input chamber in communication with each further fluid input conduits;

And a lid which seals at least the fluid input chamber and first vent hole upon closure.

Another aspect of the invention is a fluidic device and related method for passively metering a first volume of fluid from an input volume of fluid, then passively metering a second volume of fluid from the first passively metered volume of fluid, and performing at least one fluidic operation on the second metered volume of fluid. In exemplary embodiments, the metering method includes the steps of:

Inputting a volume of fluid into a sample input chamber;

At least partly filling the sample input chamber, and capillary filling the metering conduit in communication with the sample input chamber;

Passively metering the input volume of fluid to a first defined volume, with excess fluid capillary filling a first overspill conduit and being absorbed by an absorbent material in a first overspill chamber;

Passively metering a second volume of fluid from the first metered volume of fluid, with excess fluid from the second fluidic metering operation being absorbed by an absorbent material in a second overspill chamber;

Said volume of fluid defined in said first metering operation being sufficient to provide the desired volume of second metered volume of fluid and close a fluid actuated closable valve in the second overspill chamber;

Producing an air gap between the second metered volume of fluid in the metering conduit, the sample input chamber and the second overspill conduit such that the second metered volume of fluid is physically isolated from all excess fluid;

Wherein all excess fluid is absorbed by an absorbent material in either or both of the first overspill chamber and the second overspill chamber;

Configured such that when the input chamber and a first vent are sealed, at least a portion of the second metered volume of fluid may be expelled into the mixing chamber via the capillary stop;

Whereby at least one additional fluid input is used to expel the second metered volume of fluid, or any remaining second metered volume of fluid, in the metering conduit, through the capillary stop and into a mixing chamber.

The advantages of one or more embodiments of the invention include:

The ability to handle a range of fluid input volumes by passively metering a first defined volume of fluid;

The ability to passively meter a desired, defined second volume of fluid from the first metered volume of fluid;

The ability to perform at least one fluidic operation on the desired, defined second metered volume of fluid;

The ability to absorb all excess input fluid sample, thus preventing any accidental contamination of the device housing, or accidental interference with the second metered volume of fluid;

The ability to carry out a number of different fluidic operations, on the second metered volume of fluid, in series;

A reduction in the amount of reagents required to carry out complex chemical and/or biochemical reactions;

Ease of use by a semi-skilled operator;

Means of sealing the device so that biological samples and/or chemicals are enclosed within the device and do not provide a contamination hazard;

Fully integrated fluidic control mechanisms; and

Means of integrating sensors into the fluidic conduits to analyse the fluids in the microfluidic device.

BRIEF DESCRIPTION OF DRAWINGS

In the annexed drawings, like references indicate like parts or features:

FIGS. 3A-I each shows a plan view and a cross-section of an exemplary embodiment of the invention demonstrating sequential passive metering with respect to the invention.

FIGS. 5A-C show three exemplary embodiments of the invention each having a different conduit configuration.

DESCRIPTION OF REFERENCE NUMERALS

Figure 1:
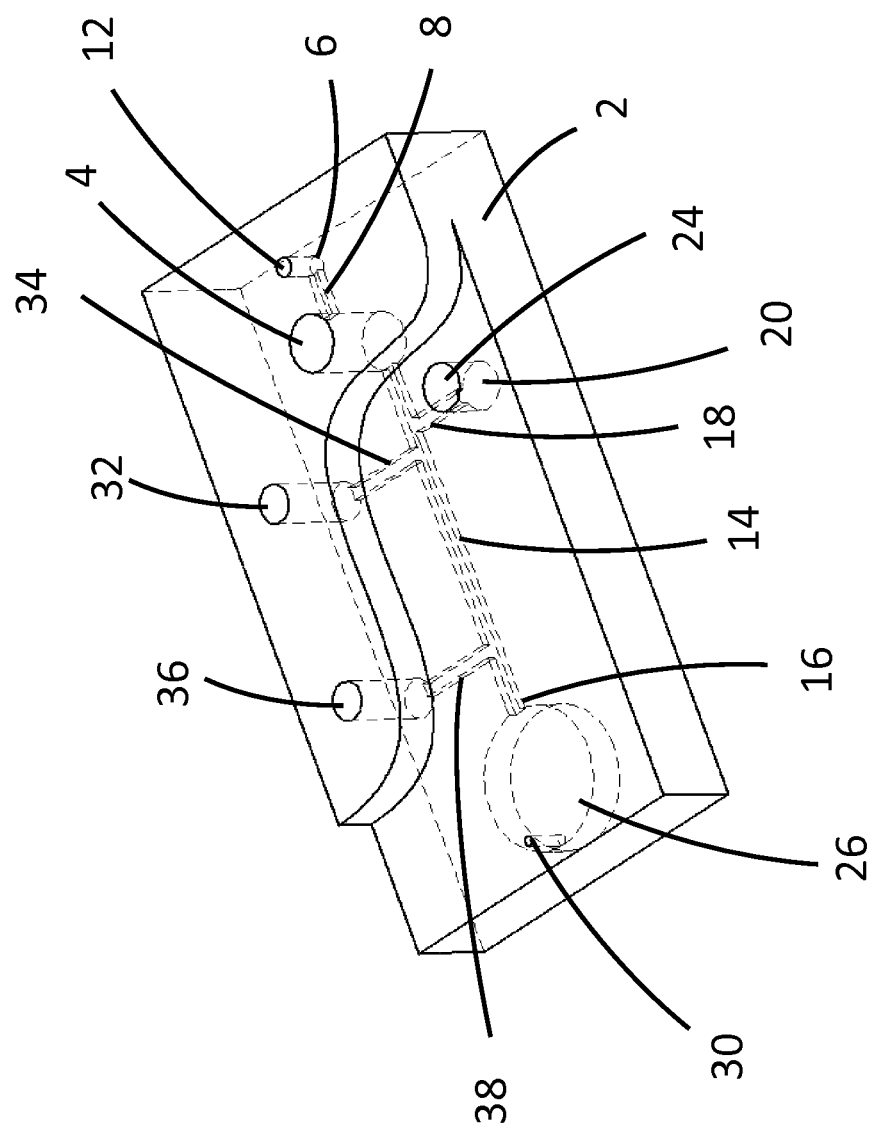
FIG. 1 shows an embodiment of an exemplary passive metering device in relation to the invention.

2 Housing
4 Sample input chamber
6 First overspill chamber
8 First overspill conduit
10 First absorbent pad
12 First vent hole
14 Metering conduit
16 Capillary stop
18 Second overspill conduit
20 Second overspill chamber
22 Second absorbent pad constituting a fluid actuated closable valve
24 Fluid actuated closable valve
26 Mixing chamber
28 Magnetic flea
30 Second vent hole
32 First fluid input chamber
34 First fluid input conduit
36 Second fluid input chamber
38 Second fluid input conduit
40 Fluid input sample
42 First metered volume of fluid 44 Second metered volume of fluid
46 Closable lid
48 First input fluid
50 Second input fluid
52 First movable piston
54 First gas chamber
56 First frangible seal
58 Second frangible seal
60 Depression head of first diameter
62 Depression head of second diameter
64 Needle/point
66 Blind fluidic conduit
68 Third fluid input chamber
70 Third fluid input conduit
72 Output conduit
74 Microfluidic cell counter
76 Hemoglobin measurement chamber
78 Waste conduit
80 Waste chamber
82 Waste vent
84 Photodiode
86 Photodetector

DETAILED DESCRIPTION OF INVENTION

The invention is a fluidic device that includes a housing, a sample input chamber, a first overspill chamber in communication with said sample input chamber, a metering conduit, a capillary stop in communication with the end of said metering conduit, a second overspill chamber in communication with said metering conduit, a mixing chamber in communication with said capillary stop and at least one additional fluid input chamber in communication with said metering conduit.

Metering is defined as the ability to accurately measure, and then isolate, a small volume of fluid from a fluid sample.

An aspect of the invention is an integrated microfluidic device for passively metering a second defined volume of fluid from a passively first metered defined volume of fluid metered from a sample input volume, absorbing all excess fluid from the metering operations in absorbent pads, and performing at least one fluidic operation on the second metered volume of fluid.

Figure 2A:
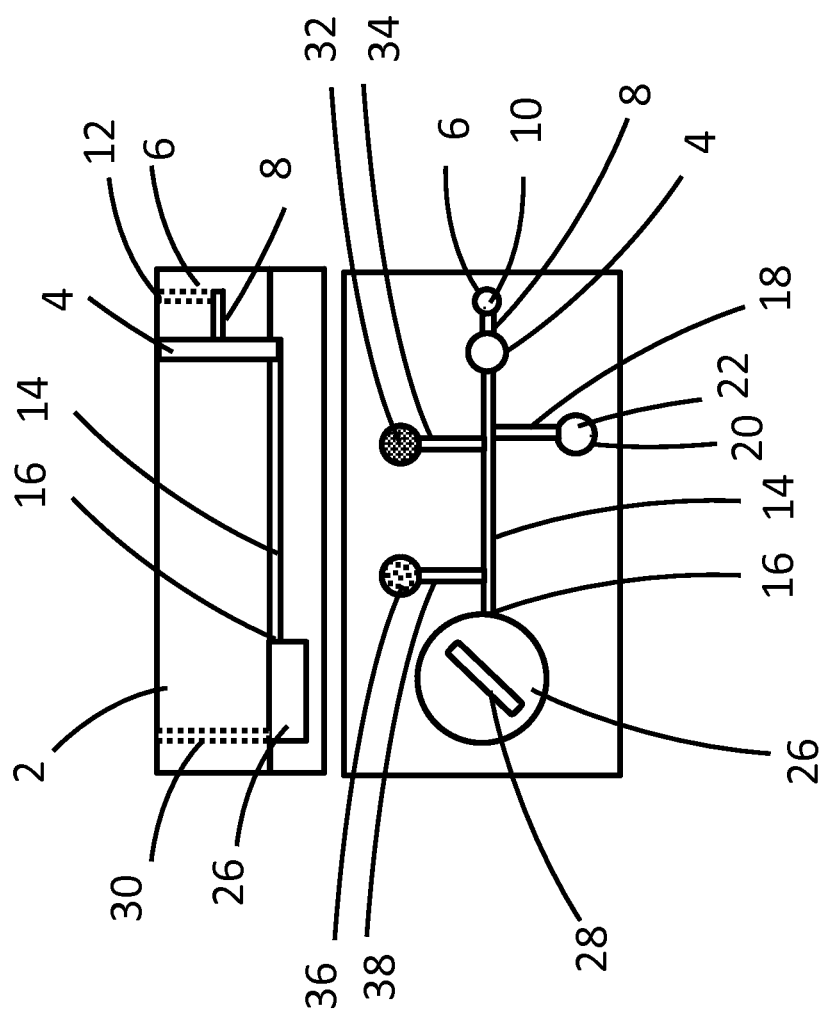
FIGS. 2A-I each shows a plan view and a cross-section of an exemplary embodiment of the invention demonstrating dynamic passive metering with respect to the invention.
Figure 2B:
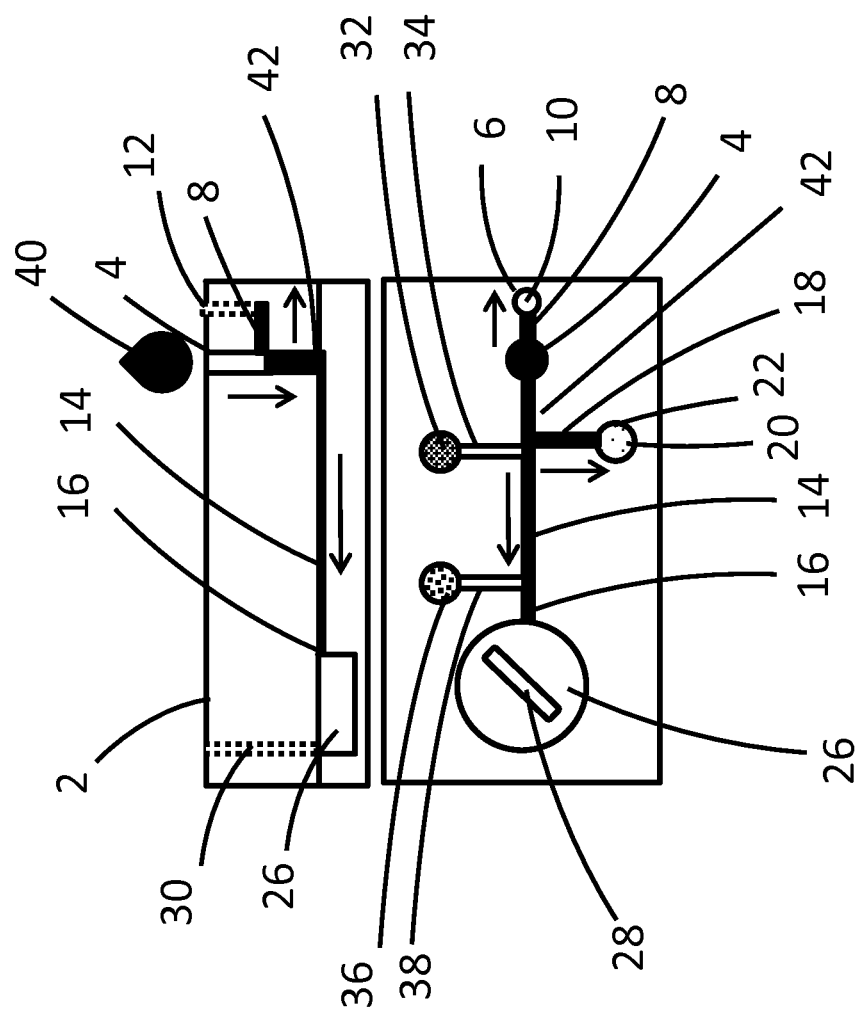
Figure 2C:
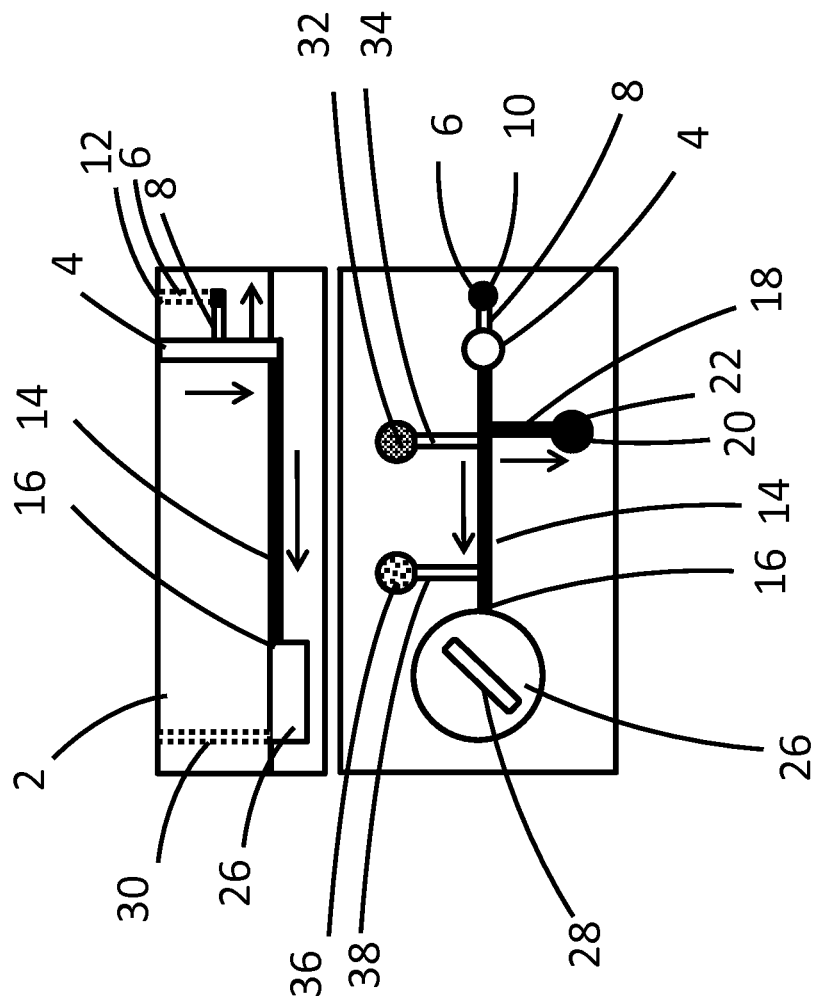
Figure 2D:
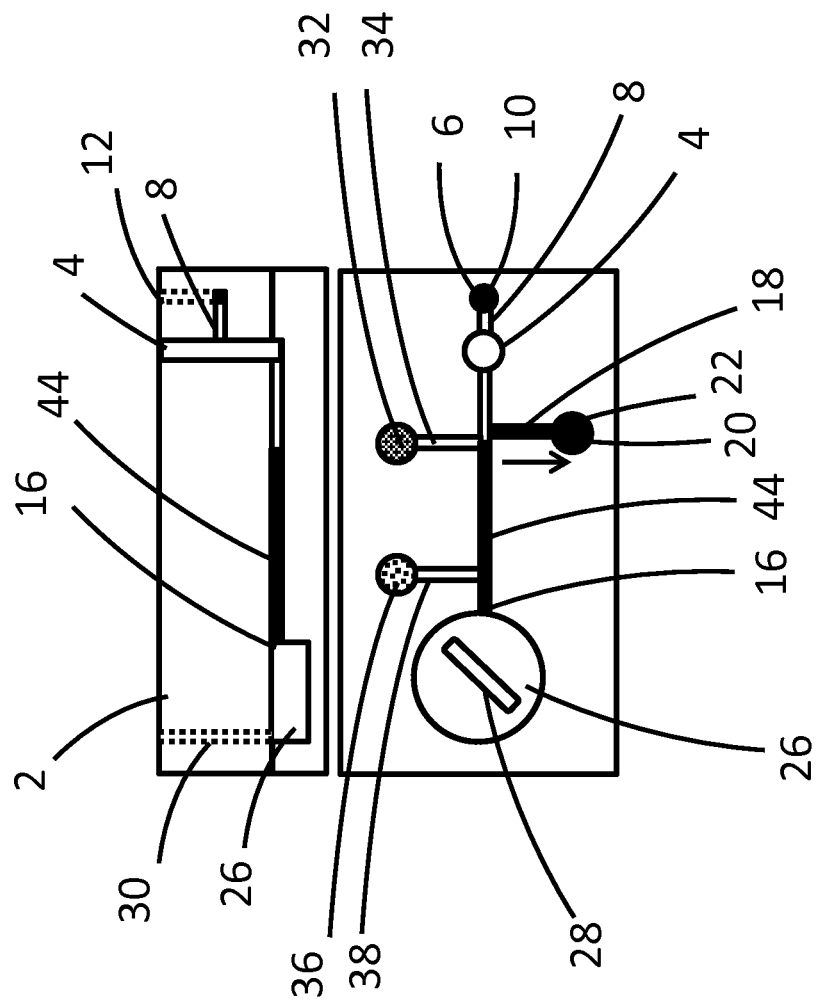
Figure 2E:
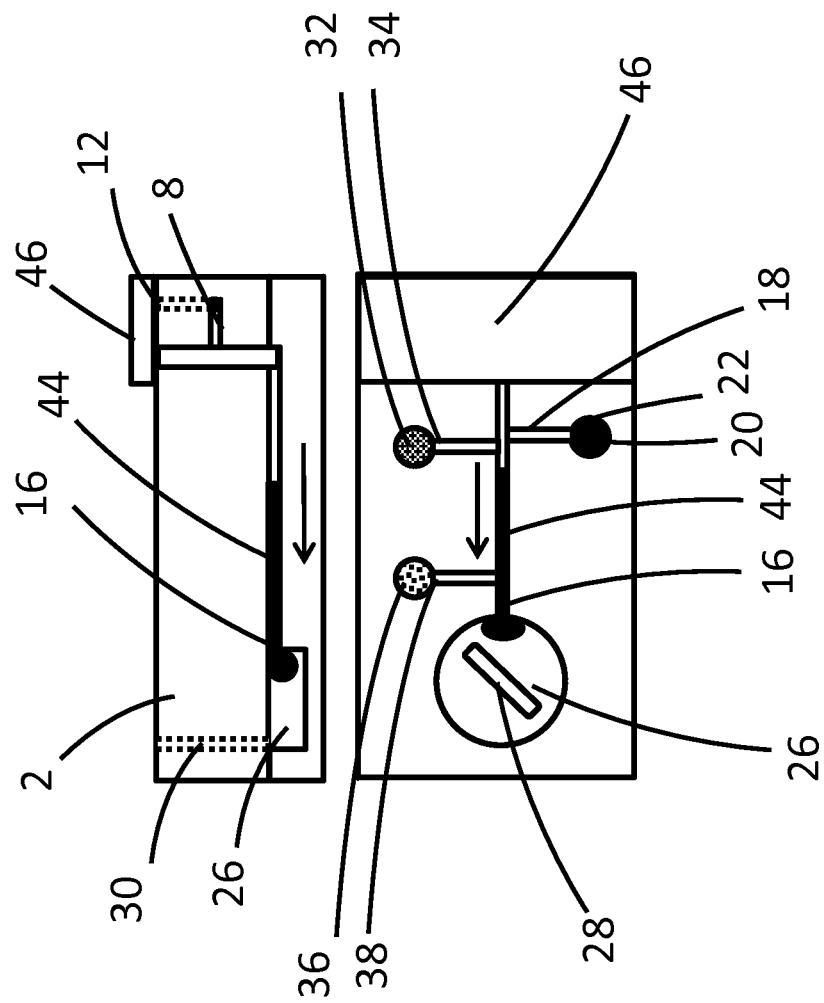
Figure 2F:
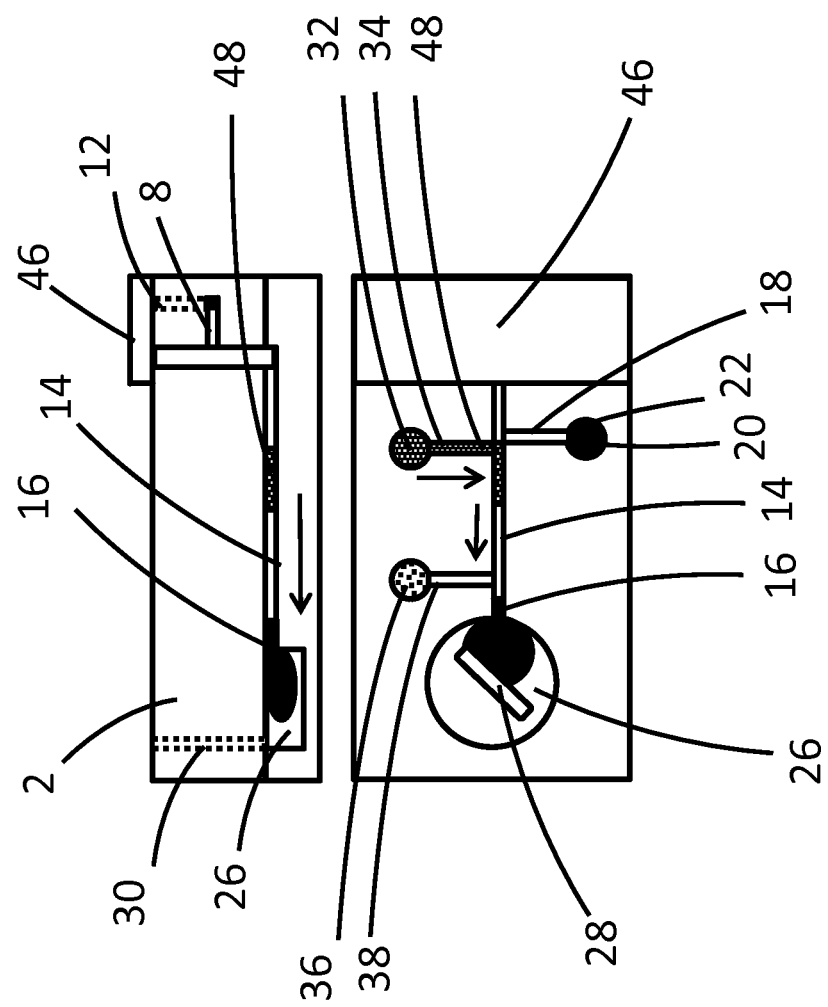
Figure 2G:
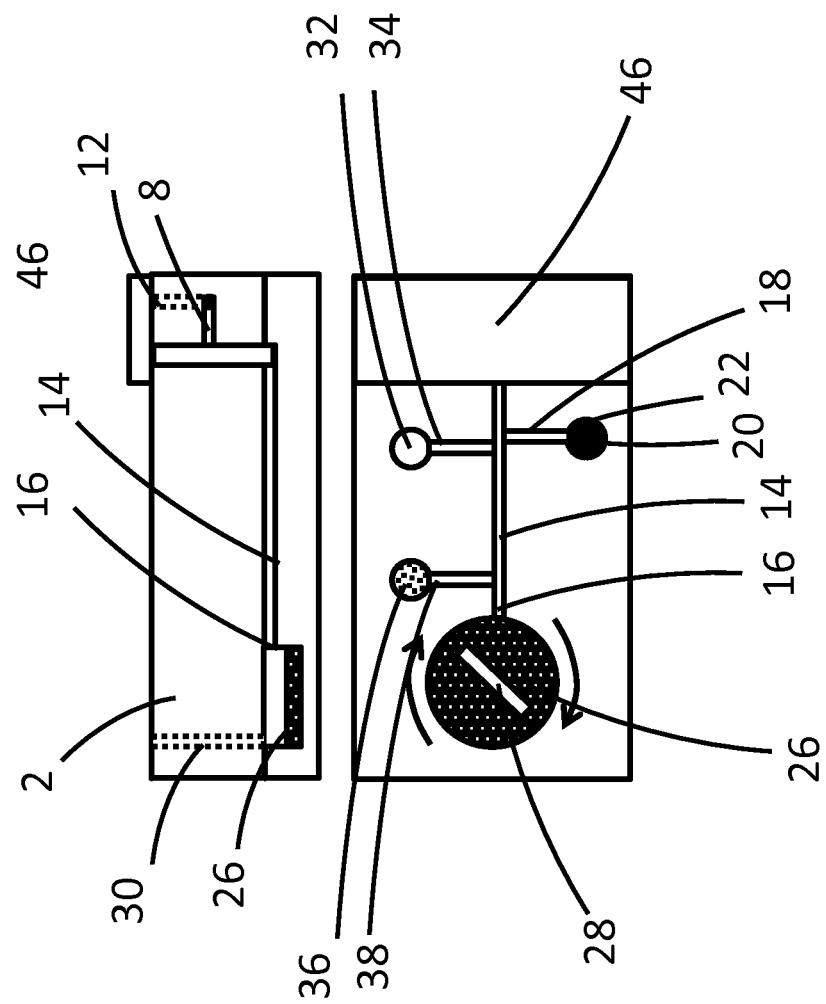
Figure 2H:
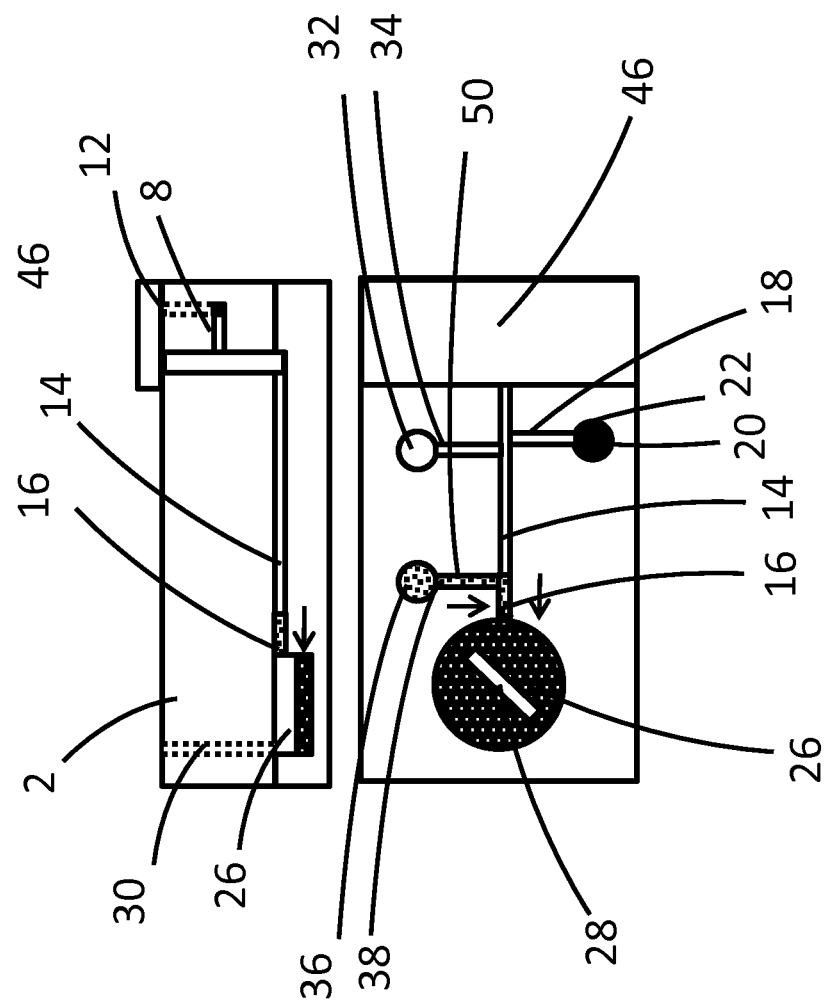
Figure 2I:
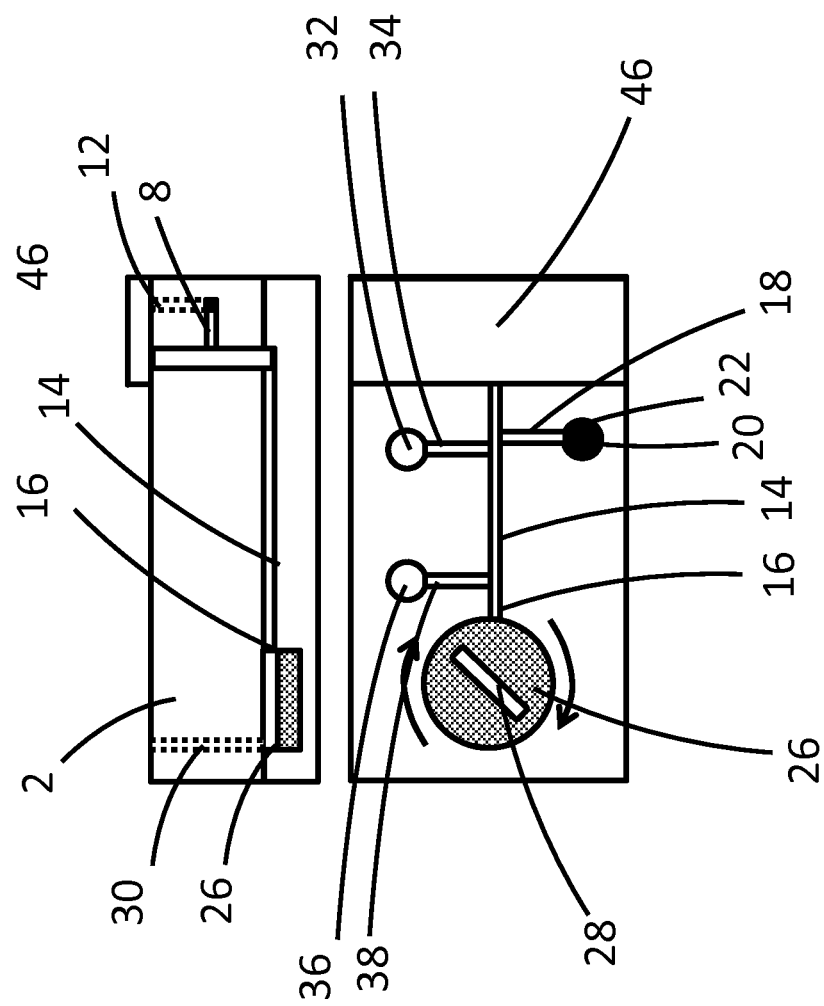

FIGS. 1-2I teaches one embodiment of the device. The housing 2 includes a sample input chamber 4 in communication with a first overspill chamber 6 via an optional, first overspill conduit 8. The first overspill chamber 6 contains a first absorbent pad 10 with a first vent hole 12. A metering conduit 14 is in communication with the base of the sample input chamber 4 and terminates in a capillary stop 16. A second overspill chamber 20 is in communication with the metering conduit 14 via an, optional, second overspill conduit 18. The second overspill chamber 20 houses a second absorbent pad 22 that acts as an exemplary fluid actuated closable valve (e.g., an embodiment of the fluid actuated closable valve 24 of FIG. 1). A mixing chamber 26 is also in communication with the end of the metering conduit 14, via said capillary stop 16, and contains a magnetic flea 28 and a second vent hole 30. A first fluid input chamber 32 and first fluid input conduit 34 are in communication with the metering conduit 14, and are positioned between the second overspill conduit 18 and the mixing chamber 26. Similarly a second fluid input chamber 36 and second fluid input conduit 38 are also in communication with the metering conduit 14, and again are positioned between the second overspill conduit 18 and the mixing chamber 26. A closable lid 46 (see FIGS. 2F-I) seals the device after completion of the metering steps.

In one embodiment, the first overspill conduit 8 and the first overspill chamber 6 are offset longitudinally from the metering conduit 14. In alternative embodiments, the first overspill conduit 8 and the first overspill chamber 6 are offset laterally from the second overspill conduit 18 and the fluid actuated closable valve 22.

The microfluidic device may be fabricated from any suitable material that is compatible with the operational fluids. Compatibility implies that the fluid does not substantially adhere or non-specifically bind to the surface of the material, and that the material is not damaged or dissolved by the fluid. Several engineering polymers may be used to fabricate the invention and include, but are not limited to, PMMA (Poly (methyl methacrylate)), PET (Polyethylene terephthalate), Polypropylene, PTFE (Polytetrafluoroethylene), and Nylon. The invention could be fabricated using any suitable manufacturing process, including injection molding, laser cutting, drilling and/or milling. Alternatively, the fluidic conduits in the housing may be patterned in resist using soft lithography techniques and processed using e.g. wet etching and/or dry etching techniques, and the like.

The absorbent pads may be fabricated from suitable absorbent material including, but not limited to gels, polymers, paper, tissue and others as may be known in the art. The material may be substantially porous, or granular in nature.

In exemplary embodiments, the absorbent pad 22 acts as the fluid closable valve. The absorbent pad 22 contains an absorbent material and an associated membrane surface, that may be in the form of an adhesive tape. For the open position of such a closable valve/absorbent pad 22, a hole is pierced in the membrane or tape, such as with a fine needle, which permits fluid flow through the second overspill conduit 18. To close the valve, that absorbent material swells upon the absorption of fluid, thereby closing the hole in the membrane and thus closing the valve to preclude additional fluid flow through the second overspill conduit. In an exemplary embodiment, the fluid actuated closable valve/absorbent pad 22 specifically is in the second overspill chamber 20.

The capillary stop 16 is a valve that prevents fluid entering the mixing chamber unless a sufficient force is applied to overcome it. In one embodiment, the capillary stop is fabricated by narrowing the metering conduit to a sufficiently small volume where it is in communication with the mixing chamber. In another embodiment, the capillary stop is achieved by applying an appropriate surface coating, such as for example a hydrophobic coating at the end of the metering conduit in communication with the mixing chamber for metering aqueous based fluids. The force of the capillary stop can usually be overcome by supplying sufficient pressure to the second metered volume of fluid.

The input and metered fluid could be chemical agents, such as for example test reagents, reducing agents, functionalized beads and the like, biological fluids such as blood, urine, saliva, DNA, and the like, environmental fluids such as for example water samples, ice core samples, or other fluids for monitoring food quality and/or food and water safety. It will be apparent that the invention can be used to carry out titrations, binding reactions, chemical functionalization processes, fluorescent labeling processes, fluid sample preparation processes, peptide synthesis processes, serial dilutions and other processes. It will be further apparent that the microfluidic device described could form part of a point-of-care diagnostics system.

Fluids can be moved around the microfluidic device using capillary forces, and/or positive and/or negative gas pressure. It will be further apparent that the fluid control mechanisms could be external to the microfluidic housing, or could be integrated into the microfluidic device housing. In one aspect of the invention, specific individual fluidic chambers within the microfluidic device could each be connected to an external gas supply to pump the fluids between chambers.

The first passive metering step has the following advantages:

It enables the device to cope with a variation in sample input volume, enabling use by unskilled operators.

It defines a volume of fluid that is sufficient to provide the desired second metered volume of fluid, seal the fluid actuated closeable valve and ensure correct operation of the device.

It ensures that any fluid in excess of that required to provide the desired second metered volume of fluid and seal the fluid actuated closeable valve, is absorbed by an absorbent material.

For example, the sample input volume may be between 10-100 ul, or a volume between 15-80 ul, or a volume between 15-60 ul, or a volume between 15-40 ul. The first passive metering operation may define a volume of fluid between 10-40 ul, or a volume between 10-30 ul, or a volume between 10-20 ul, or a volume between 5-10 ul, respectively based on the sample input volume.

The second passive metering step has the following advantages:

It ensures that the defined second volume of fluid is isolated from all the excess input fluid.

It closes the fluid actuated closable valve.

It enables additional fluidic operations to be carried out on the second passively metered sample of fluid.

It prevents any backflow of the defined metered second volume of fluid back into the device or into the second absorbent pad.

The second passive metering operation may meter a volume of fluid between 0.1-30 ul, or a volume between 0.1-20 ul, or a volume between 0.5-10 ul, or a volume between 0.5-5 ul, respectively based on the sample input volume and/or first passively metered fluid volume. The second passively metered volume of fluid may be substantially equivalent to the volume of the metering conduit between, and including, the capillary stop and the second overspill conduit.

In exemplary embodiments, at least one fluidic operation can be performed on the second metered volume of fluid. The fluidic operations may include, but are not limited to, any combination of mixing, labeling, staining, incubating, lysing, quenching, titrating, separating or diluting.

In exemplary embodiments, at least two further fluidic operations can be performed, in series, on the second metered volume of fluid. The fluidic operations may include, but are not limited to, any combination of mixing, labeling, staining, incubating, lysing, quenching, titrating, separating or diluting.

Labelling is defined as the process of adding a, preferably fluorescent or radioactive, marker to, for example, a cell, bead, or other biological entity.

Incubating is defined as providing favourable conditions for specific processes, such as for example, fluorescent labelling of blood cells, to take place.

Lysing is defined as the destruction or dissolution of cells, preferably by chemical and/or mechanical means.

Quenching is defined as the halting, stopping or significant reduction in the rate of lysing, preferably by chemical means.

Titrating is defined as the process carried out to ascertain the concentration of a given analyte (preferably with some indicator fluid) by adding a titrant solution of known concentration in small volumes, and measuring the volume of titrant required to convert the analyte (or indicator) to a different form.

Separating is defined as sorting or isolating different components, or elements, within a fluid sample. This may be achieved using, for example, magnetic beads and magnets, or covalent attachment.

An aspect of the invention, therefore, is an integrated fluidic device. In exemplary embodiments, the integrated fluidic device includes a sample fluid input chamber that provides an input of a sample fluid, and a first overspill chamber in fluid communication with the fluid input chamber. A metering conduit is in fluid communication with the fluid input chamber and the first overspill chamber, wherein the metering conduit meters a first metered volume of fluid from the sample fluid, and the first overspill chamber receives fluid from the sample fluid in excess of the first metered volume of fluid. A second overspill chamber is in fluid communication with the metering conduit, wherein the metering conduit meters a second metered volume of fluid from the first metered volume of fluid, and the second overspill chamber receives fluid from the first metered volume of fluid in excess of the second metered volume of fluid.

FIGS. 2A-I teach one embodiment in which a first metered volume of fluid 42 and a second metered volume of fluid 44 are metered dynamically; the second metered volume of fluid 44 is then mixed with two further separate fluid input samples 48, 50 in the mixing chamber 26. In this embodiment, the fluid actuated closable valve 22 is set to the open position before fluid is input into the device (e.g., the hole in the valve membrane described above may be pre-pierced). FIG. 2A shows a cross-section and a plan view of the integrated microfluidic device including a housing 2, a sample input chamber 4 in communication with a first overspill chamber 6 via a first overspill conduit 8. A first absorbent pad 10 is contained within the first overspill chamber 6 which is in further communication with a first vent hole 12. A metering conduit 14 is in communication with the base of the sample input chamber 4 and terminates in a capillary stop 16 at the mixing chamber 26. A second overspill chamber 20 is in communication with the metering conduit 14 via a second overspill conduit 18. The second overspill chamber 20 houses a second absorbent pad 22 that acts as the fluid actuated closable valve. The mixing chamber 26 contains a magnetic flea 28 and a second vent hole 30. A first fluid input chamber 32 and first fluid input conduit 34 are in communication with the metering conduit 14, and are positioned between the second overspill conduit 18 and the mixing chamber 26. Similarly, a second fluid input chamber 36 and second fluid input conduit 38 are also in communication with the metering conduit 14, and again are positioned between the second overspill conduit 18 and the mixing chamber 26.

In FIG. 2B, a fluid input sample 40 is introduced to the integrated microfluidic device housing 2 via the sample input chamber 4. The fluid input sample 40 fills the sample input chamber 4 and capillary fills, at least a portion of, the first overspill conduit 8, and the metering conduit 14 to meter the first metered volume of fluid 42. The fluid input sample 40 may also start to capillary fill at least a portion of the second overspill conduit 18. The fluid input sample 40 will not capillary fill the first fluid input conduit 34 or the second fluid input conduit 38, as these conduits are essentially sealed at their input ports, the first fluid input chamber 32 and the second fluid input chamber 36, by movable pistons (not shown for clarity). Excess fluid input sample capillary fills the first overspill conduit 8 and is absorbed by the first absorbent pad 10. The first metered volume of fluid 42 provides enough fluid for the required second metered volume of fluid 44 and to close the fluid actuated closable valve 22.

FIG. 2C illustrates that once the first metered volume of fluid 42 has fully capillary filled the metering conduit 14 down to the capillary stop 16, the excess fluid from the first metered volume of fluid 42 fully capillary fills the second overspill conduit 18, and is absorbed by the second absorbent pad 22. Accordingly, to permit metering of the second metered volume of fluid, the absorbent pad/closeable valve 22 is initially open when the metering conduit meters the first metered volume of fluid. and once the metering conduit meters the second metered volume of fluid, the closeable valve closes as the second overspill chamber receives the fluid in excess of first metered volume of fluid to meter the second metered volume of fluid.

In this manner, the first and second metering operations are dynamic in the sense that there essentially is no precise distinction or boundary between the first metering operation finishing and the second metering operation beginning. In other words, the second overspill conduit 18 and second overspill chamber 20 fill at the same time as the filling of the first overspill conduit 8 and first overspill chamber 6. This dynamic operation does not require any intervention by the operator to complete the second metering operation.

FIG. 2D shows where the fluid in the metering conduit 14 splits at the junction with the second overspill conduit 18 leaving a defined second metered volume of fluid 44. All the excess fluid from the first metered volume of fluid 42 is absorbed by the second absorbent pad 22 constituting the fluid actuated closable valve, which then closes such fluid actuated closable valve. The second metered volume of fluid 44 is thus completely isolated from all excess input fluid, and all the excess fluid is held in one of two absorbent pads thus preventing any contamination.

In FIG. 2E, the closable lid 46 is closed sealing both the sample input chamber 4 and the first vent hole 12. In the process of closing the closable lid 46 over the first vent hole and the sample input chamber, at least a portion of the second metered volume of fluid 44 is forced into the mixing chamber 26.

The device may include at least one further fluid input chamber in fluid communication with the metering conduit, wherein the mixing chamber receives a further fluid from the at least one further fluid input chamber through the metering conduit and the capillary stop. The at least one further fluid chamber includes a pressure displacement mechanism for transferring the further fluid from the at least one further fluid chamber into the metering conduit. There may be "n" further fluid input chambers, where n is greater than or equal to two. For example, a first moveable piston, omitted for clarity, is positioned in the first fluid input chamber 32 with a defined volume of gas between the base of the moveable piston and a defined volume of first input fluid 48 (see FIG. 2F). The first moveable piston is depressed, injecting the first input fluid 48 along the first fluid input conduit 34, along the metering conduit 14 and into the mixing chamber 26 as depicted in FIG. 2F. The first input fluid 48 acts to flush the second metered volume of fluid 44 through the capillary stop 16 and into the mixing chamber 26. Fully depressing the first moveable piston ensures that the first input fluid 48 is fully injected into the mixing chamber 26. The second metered volume of fluid 44 and the first input fluid 48 are then mixed for a predetermined length of time using a magnetic flea 28 in the mixing chamber 26, as depicted in FIG. 2G. A second input fluid may then be introduced to the mixing chamber 26. In particular, FIG. 2H teaches how depressing a second movable piston, omitted for clarity, forces a second input fluid 50 along the second fluid input conduit 38 and the metering conduit 14 and into the mixing chamber 26. The second input fluid 50 can then be mixed with the second metered volume of fluid 44 and the first input fluid 48 that are already in the mixing chamber 26 using the magnetic flea 28, as depicted in FIG. 2I.

FIGS. 3A-I teach one embodiment in which the first metered volume of fluid 42 and the second metered volume of fluid 44 are passively metered sequentially; the second metered volume of fluid 44 input sample is then mixed with two further separate fluid input samples 48, 50 in the mixing chamber 26. In this embodiment, the fluid actuated closable valve is set to the closed position before fluid is input into the device (e.g., the hole in the valve membrane described above is not pre-pierced as done in the FIG. 2 embodiment).

Figure 3A:
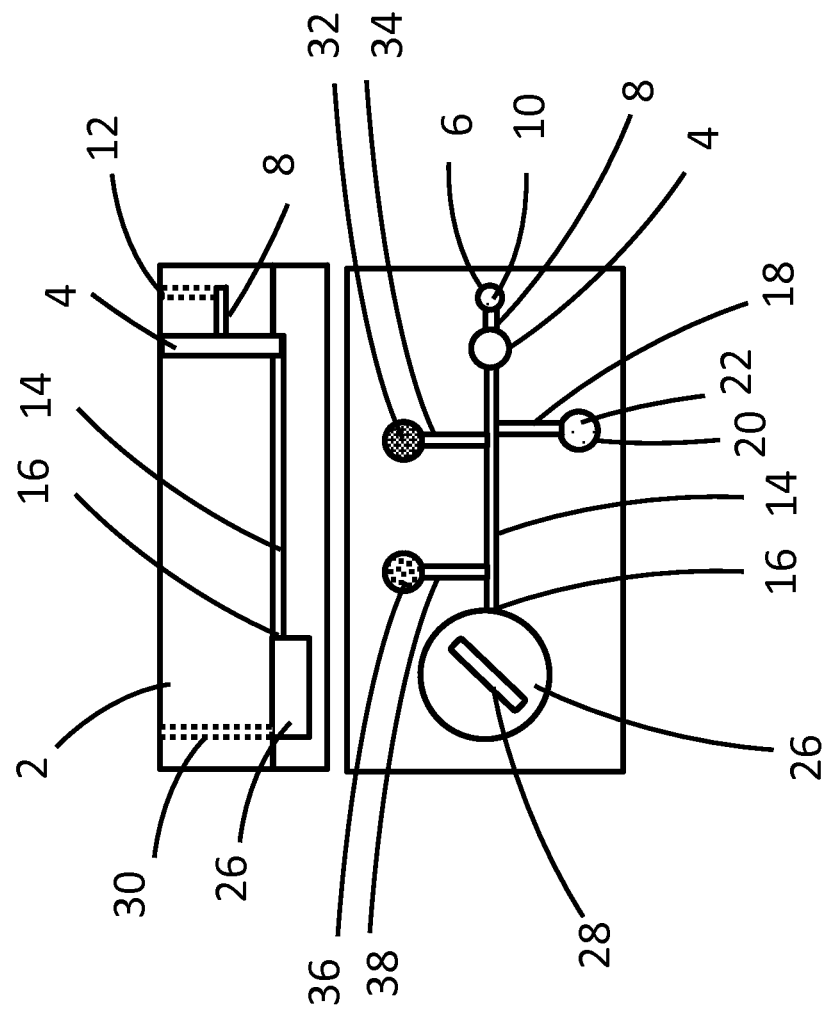

FIG. 3A shows a cross-section and a plan view of the integrated microfluidic device including a housing 2, a sample input chamber 4 in communication with a first overspill chamber 6 via a first overspill conduit 8. A first absorbent pad 10 is contained within the first overspill chamber 6, which is in further communication with a first vent hole 12. A metering conduit 14 is in communication with the base of the sample input chamber 4 and terminates in a capillary stop 16 at the mixing chamber 26. A second overspill chamber 20 is in communication with the metering conduit 14 via a second overspill conduit 18. The second overspill chamber 20 houses a second absorbent pad 22 that acts as a fluid actuated closable valve. In this embodiment, the fluid actuated closable valve 22 is sealed, or closed, e.g. the membrane is not pierced to have a vent hole prior to initiating the metering operations. The mixing chamber 26 contains a magnetic flea 28 and a second vent hole 30. A first fluid input chamber 32 and first fluid input conduit 34 are in communication with the metering conduit 14, and are positioned between the second overspill conduit 18 and the mixing chamber 26. Similarly a second fluid input chamber 36 and second fluid input conduit 38 are also in communication with the metering conduit 14, and again are positioned between the second overspill conduit 18 and the mixing chamber 26.

Figure 3B:
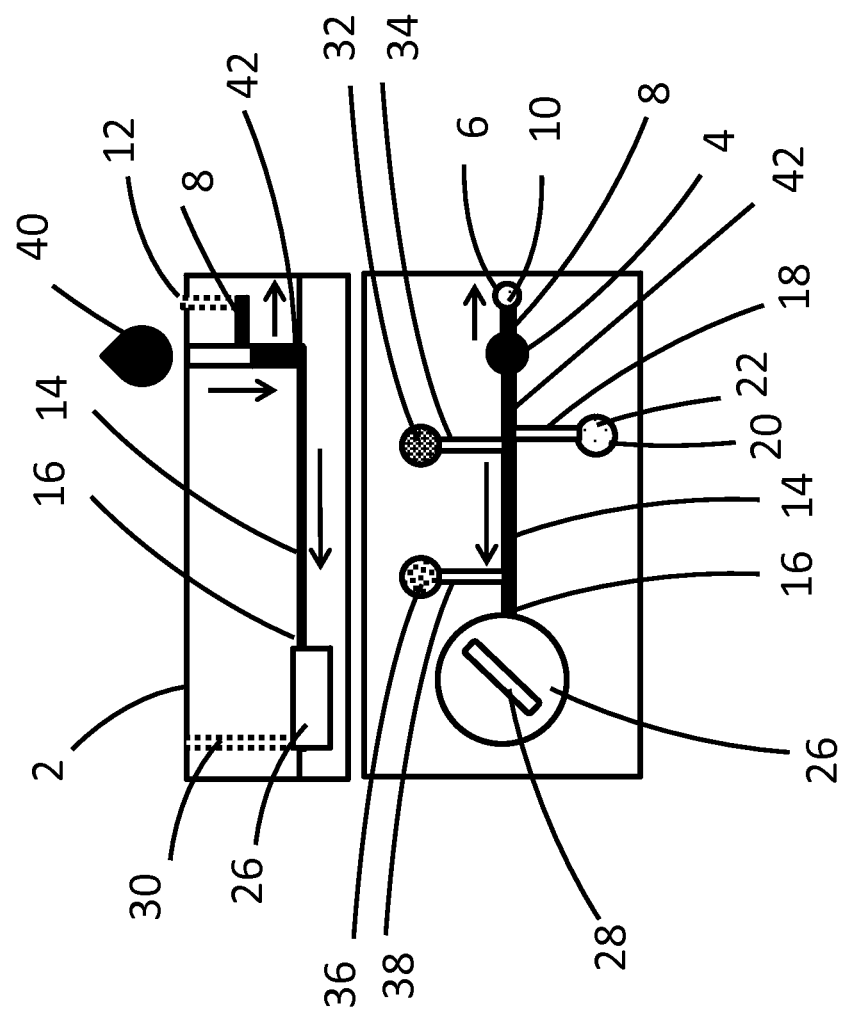

In FIG. 3B, a fluid input sample 40 is introduced to the integrated microfluidic device housing 2 via the sample input chamber 4. The fluid input sample 40 fills the sample input chamber 4 and capillary fills the first overspill conduit 8, and the metering conduit 14 to meter the first metered volume of fluid 42. The fluid input sample 40 will not capillary fill the second overspill conduit 18, as the fluid actuated closable valve 22 is closed. The fluid input sample 40 will also not capillary fill the first fluid input conduit 34 or the second fluid input conduit 38, as these conduits are essentially sealed at their input ports, the first fluid input chamber 32 and the second fluid input chamber 36, by movable pistons (not shown for clarity). Excess fluid input sample capillary fills the first overspill conduit 8 and is absorbed by the first absorbent pad 10. The membrane closing the fluid closable valve 24 is then pierced by the operator, or opened, as to create a vent hole at the fluid actuated closable valve which opens the valve. The first metered volume of fluid 42 provides enough fluid for the required second metered volume of fluid and to close the fluid actuated closable valve 24 after it has been opened.

Figure 3C:
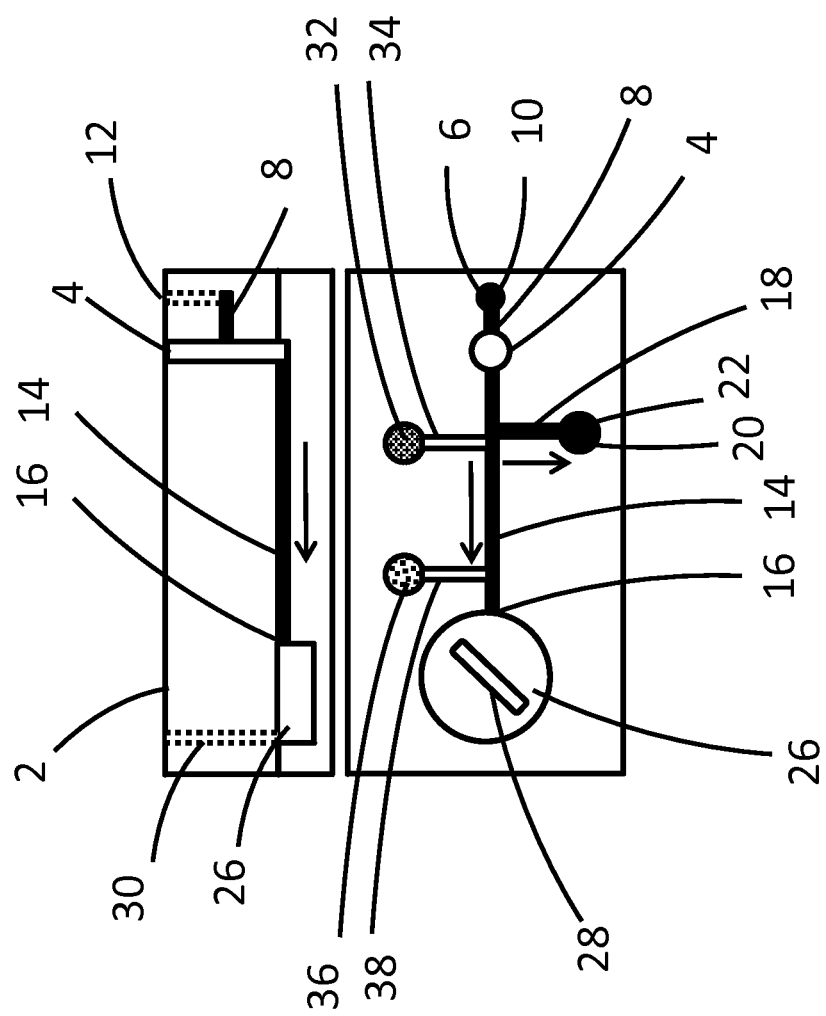
Figure 3D:
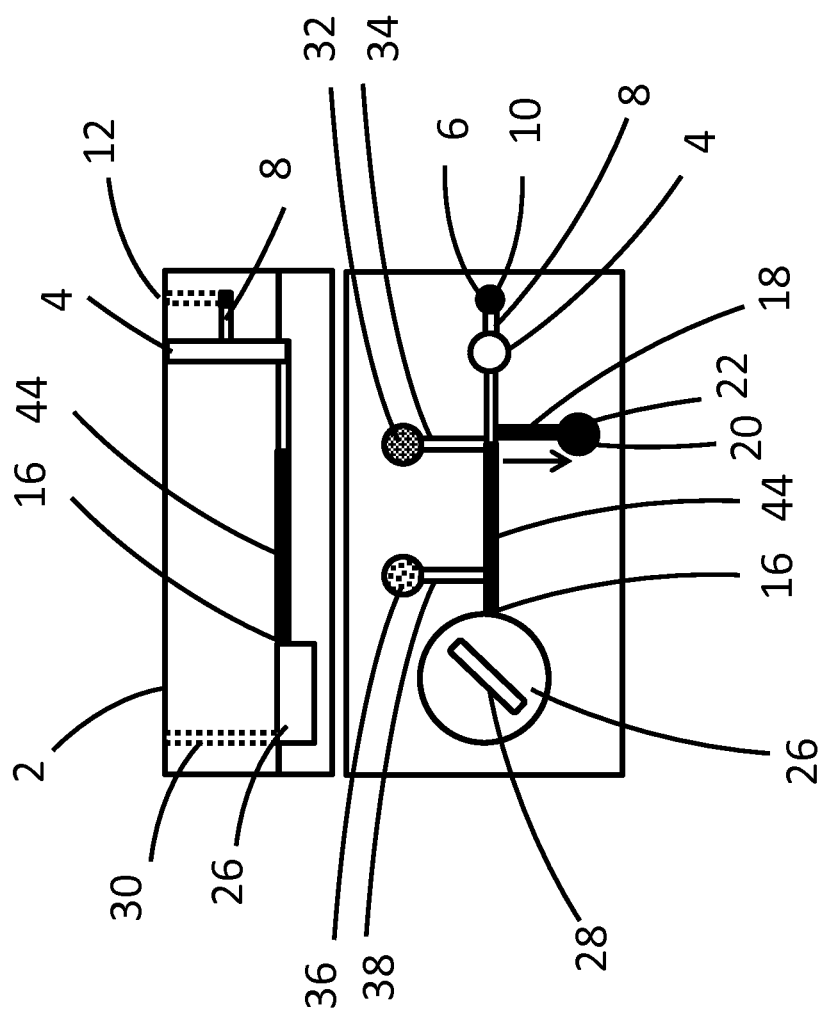

FIG. 3C illustrates that once a vent has been created at the fluid actuated closable valve 22, the excess fluid from the first metered volume of fluid 42 fully capillary fills the second overspill conduit 18, and is absorbed by the second absorbent pad/closable valve 22. FIG. 3D shows where the fluid in the metering conduit 14 splits at the junction with the second overspill conduit 18 leaving a defined second metered volume of fluid 44. Excess fluid from the first metered volume of fluid 42 is absorbed by the second absorbent pad/closable valve 22, which closes such fluid actuated closable valve. The second metered volume of fluid 44 is thus completely isolated from all excess input fluid, and all the excess fluid is held in one of two absorbent pads thus preventing any contamination.

In this manner, the first and second metering operations are sequential in the sense that there essentially is a precise distinction or boundary between the first and second metering operations, such that first metering operation is completed entirely before beginning the second metering operation. In other words, the second overspill conduit 18 and second overspill chamber 20 do not fill at the same time as the filling of the first overspill conduit 8 and first overspill chamber 6. This sequential operation requires that the operator open to fluid closable valve (e.g., by piercing the valve membrane) to initiate and perform the second metering operation.

Figure 3F:
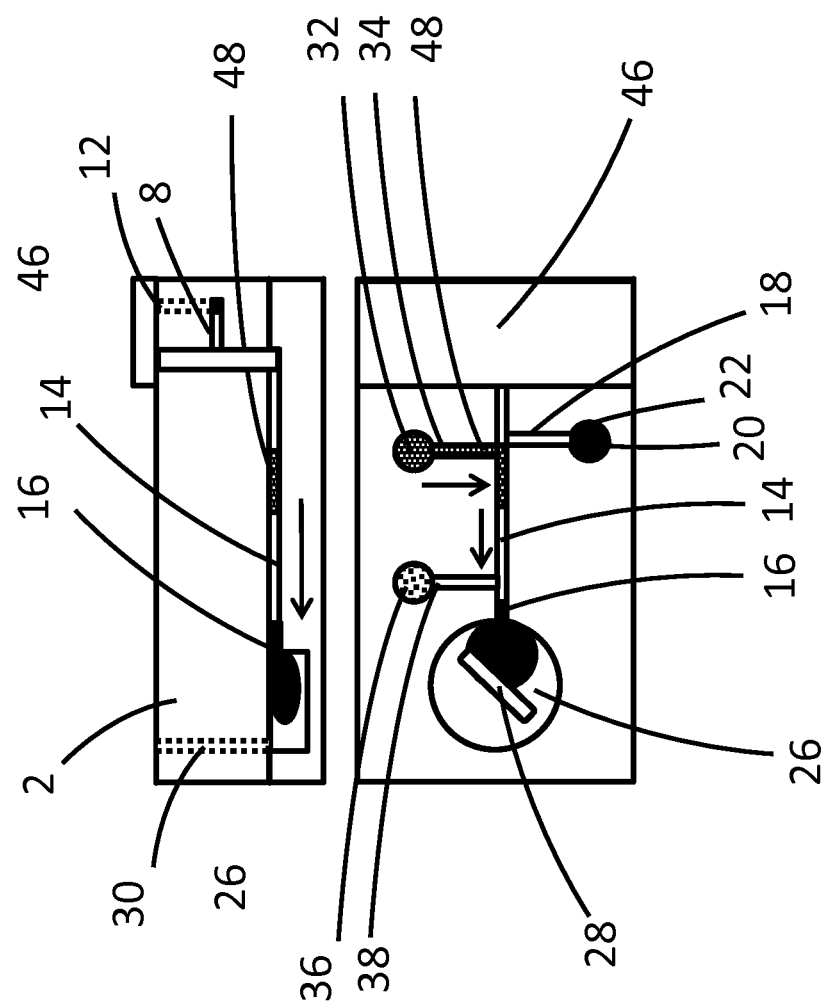
Figure 3G:
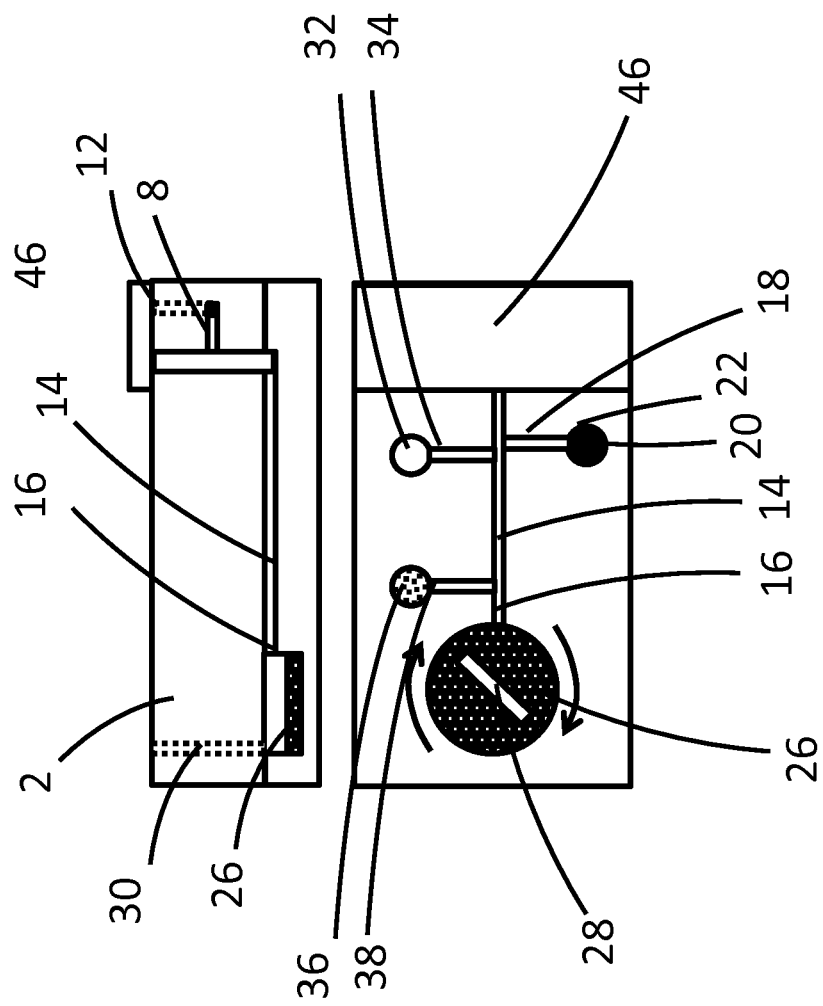

In FIG. 3E, the closable lid 46 is closed sealing both the sample input chamber 4 and the first vent hole 12. In the process of closing the closable lid 46, at least a portion of the second metered volume of fluid 44 may enter the mixing chamber 26. A first moveable piston, omitted for clarity, is positioned in the first fluid input chamber 32 with a defined volume of gas between the base of the moveable piston and the defined volume of first input fluid 48 (see FIG. 3F). The first moveable piston is depressed, injecting the first input fluid 48 along the first fluid input conduit 34, along the metering conduit 14 and into the mixing chamber 26 as depicted in FIG. 3F. The first input fluid 48 acts to flush the second metered volume of fluid 44 through the capillary stop 16 and into the mixing chamber 26. Fully depressing the first moveable piston ensures that the first input fluid 48 is fully injected into the mixing chamber 26. The second metered volume of fluid 44 and the first input fluid 48 are then mixed for a predetermined length of time using a magnetic flea 28 in the mixing chamber 26, as depicted in FIG. 3G.

Figure 3H:
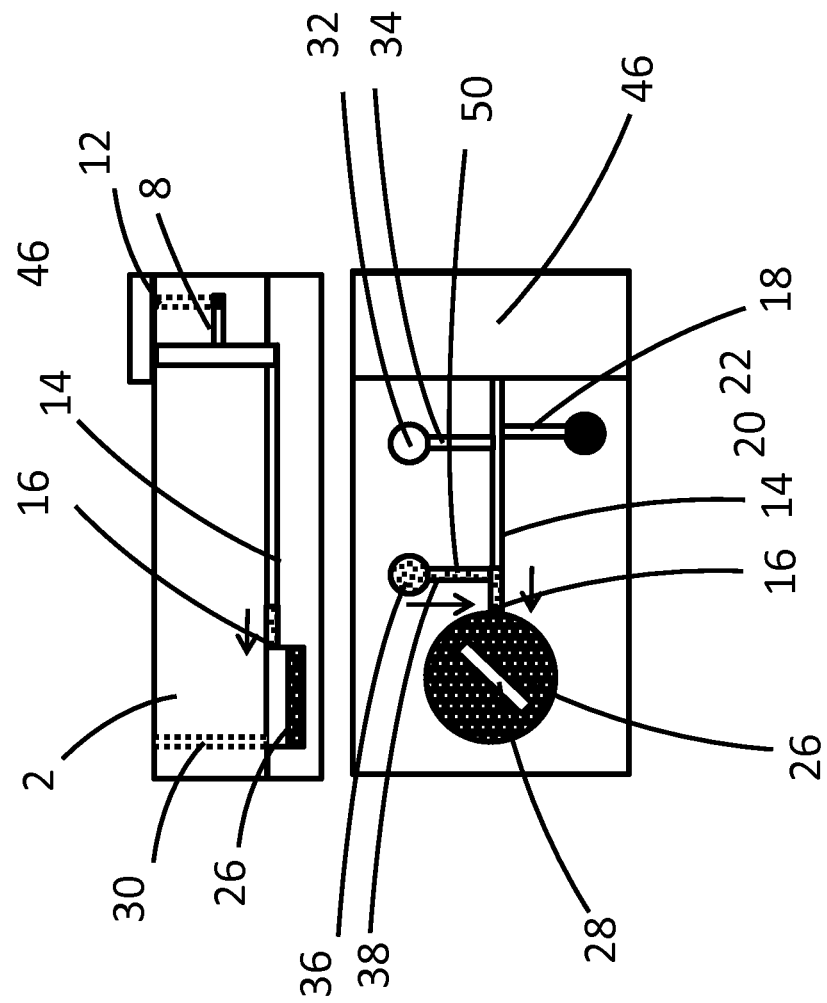
Figure 3I:
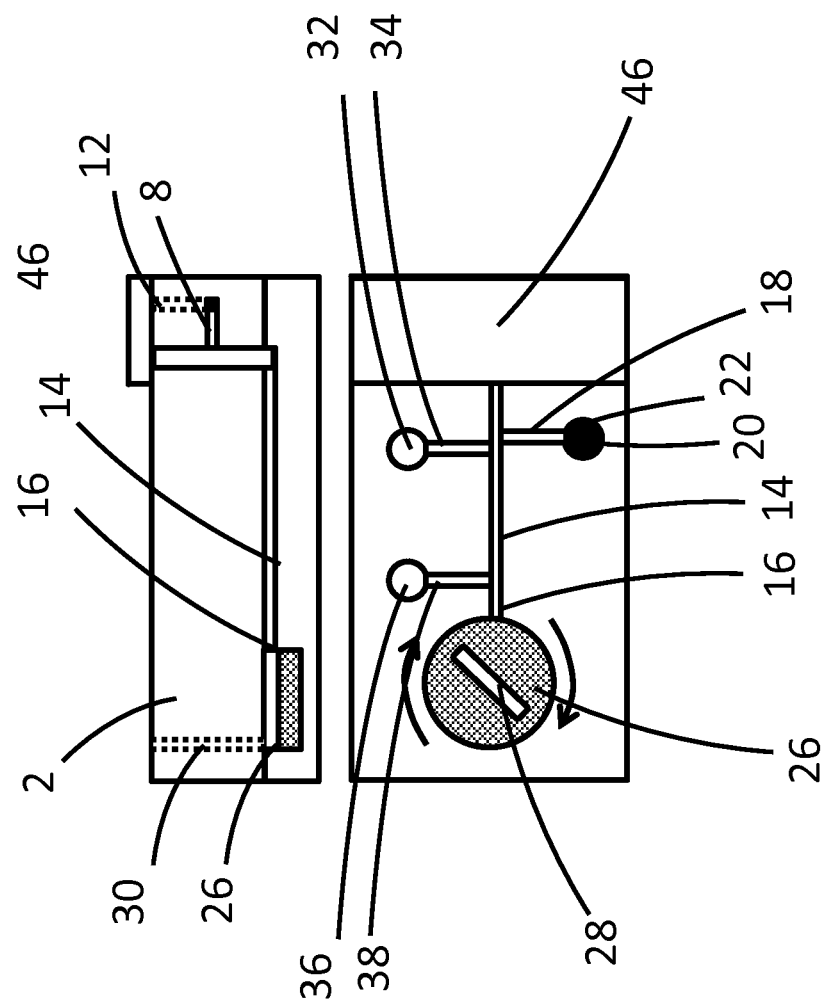

A second input fluid may then be introduced to the mixing chamber 26. FIG. 3H teaches how depressing a second movable piston, omitted for clarity, forces a second input fluid 50 along the second fluid input conduit 38 and the metering conduit 14 and into the mixing chamber 26. The second input fluid 50 can then be mixed with the second metered volume of fluid 44 and the first input fluid 48 that are already in the mixing chamber 26 using the magnetic flea 28, FIG. 3I.

In a further aspect of the invention, a magnetic flea is used to mix, and/or lyse fluids in the mixing chambers. For the most effective mixing and/or lysing conditions in a fluidic chamber with a magnetic flea to be realized, the volume of fluid in the fluidic chamber, the geometry of the mixing well, the size of the magnetic flea, and the rotational velocity of the magnetic flea all have to be optimized.

The "aspect ratio" of the volume of fluid within the fluidic chamber is defined as the ratio of the height of fluid in the chamber to the width of fluid in the chamber. Lower aspect ratios are associated with more efficient lysing and/or mixing. In a specific embodiment of the invention, the lysing and/or mixing fluidic chambers may have an aspect ratio between 0.1 and 4. Preferably the aspect ratio will be between 0.1 and 2, and more preferably between 0.2 and 0.95.

The edge of the magnetic flea may be flush against the internal wall of the mixing chamber, or may be spaced away from the wall of the mixing chamber. In a specific embodiment, the ratio of the length of the magnetic flea to the diameter of the mixing chamber is preferably greater than 0.5, and more preferably greater than 0.6, and most preferably greater than 0.7.

In a specific embodiment, the ratio of the height of the fluid to the height of the magnetic flea will preferably be at least 1.

The faster the magnetic flea rotates, the more efficient the mixing and/or lysing. Preferably, in one embodiment, the magnetic flea will rotate at greater than 300 rpm, more preferably greater than 500 rpm, and most preferably at 1400 rpm.

It will be appreciated by one skilled in the art that the invention could be configured to carry out any given or particular fluidic process in duplicate, triplicate, or quadruplicate and so on, or to perform at least one sample measurement and a control measurement.

In exemplary embodiments, the device may be configured such that when the closable lid is closed, the sample input chamber, the first vent and the fluid actuated closable valve are all sealed.

In exemplary embodiments, the aspect ratios of the metering conduit, the first overspill conduit, and the second overspill conduit are designed as to preferentially capillary fill the metering conduit, followed by the first overspill conduit, then the second overspill conduit. Typically, narrower channels capillary fill faster than wider channels.

Fluids can be moved around the microfluidic device using capillary forces, and/or positive and/or negative gas pressure, and/or positive and/or negative displacement pressure. It will be further apparent that the fluid control mechanisms could be external to the microfluidic housing, or could be integrated into the microfluidic device housing. In one exemplary embodiment of the invention, specific individual fluidic chambers within the microfluidic device could each be connected to an external gas supply to pump the fluids between chambers.

Figure 4A:
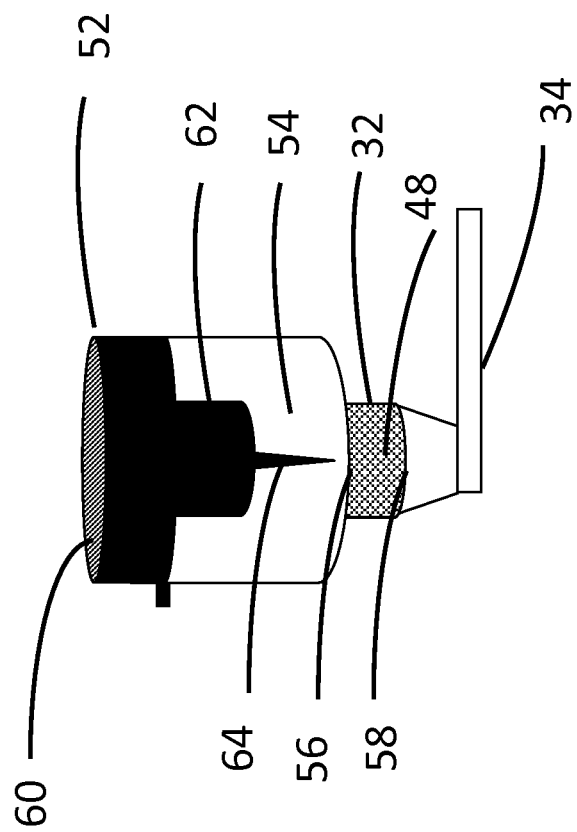
FIG. 4A-B each shows a cross-section of an exemplary embodiment of fluidic chamber geometries demonstrating integrated fluid control with respect to the invention.
Figure 4B:
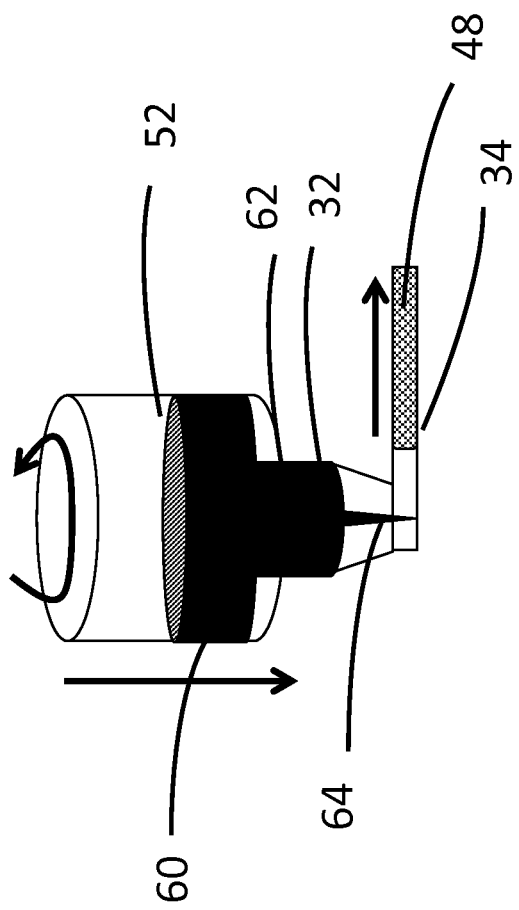

FIGS. 4A-B illustrate one embodiment of a displacement pressure mechanism that could be integrated into any additional fluid input chamber to introduce fluid to the mixing chamber, and may be employed in the embodiments of Figure sets 2 and 3. FIG. 4A teaches the initial configuration of such a displacement pressure mechanism, with the first displacement pressure mechanism including a first movable piston 52, a first gas chamber 54, a first fluid input chamber 32 and a first fluid input conduit 34. The first fluid input chamber 32 contains a defined volume of the first input fluid 48 (see Figure sets 2 and 3). In an exemplary embodiment, the defined volume of first input fluid 48 would be sealed in the first fluid input chamber 32 between a first frangible seal 56 and a second frangible seal 58. The first movable piston 52 includes a depression head of a first diameter 60 to fit the diameter of the first gas chamber 54, a depression head of a second diameter 62 to fit the diameter of the fluid input chamber 32, and a needle or point 64 capable of piercing the first frangible seal 56 and the second frangible seal 58. The first movable piston 52 would also include a locking mechanism to prevent accidental depression of the displacement pressure mechanism. In FIG. 4B, the movable piston 52 is rotated to unlock the locking mechanism, and then depressed. Depressing the movable piston 52 pierces the first 56 and second 58 frangible seals, and the defined volume of gas contained within the first gas chamber 54 forces the defined volume of first input fluid 48 out of the first fluid input chamber 32, along the first fluid input conduit 34, along the metering conduit 14 and ultimately into the mixing chamber 26 as described above.

In a further embodiment of the invention, the volume of gas in the first gas chamber 54 can be designed to hold a desired volume of gas. The defined volume of gas should be sufficient to force the defined volume of first input fluid 48 out of the fluid input chamber 32, along the fluid input conduit 34, through the metering conduit 14 and into the mixing chamber 26.

In one embodiment, the volume of the fluidic chambers can be designed to be as small as 5 ul or as large as 10 ml. In another embodiment, the volume of a fluidic chamber may be between 5 ul and 3 ml, and in yet a further embodiment the volume of a fluidic chamber may be between 5 ul and 500 ul. The different fluidic chambers in a single microfluidic device do not need to be the same volume, and the volumetric design of each fluidic chamber can be optimized for any given or particular application.

It will be apparent to one skilled in the art that not all of the fluidic chambers need to be of the same volume, and that the geometries of the chambers and/or displacement pressure mechanisms can be designed as to best accommodate (a) the volume fluid that a chamber is pre-loaded with and/or (b) the volume of fluid that needs to be moved within the device.

Figure 5B:
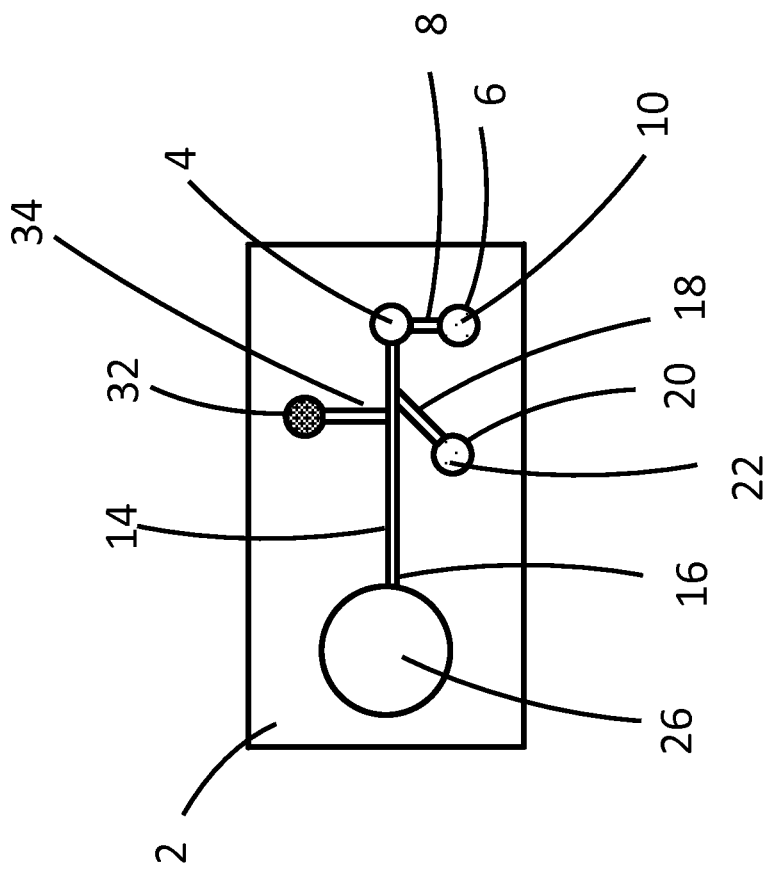
Figure 5C:
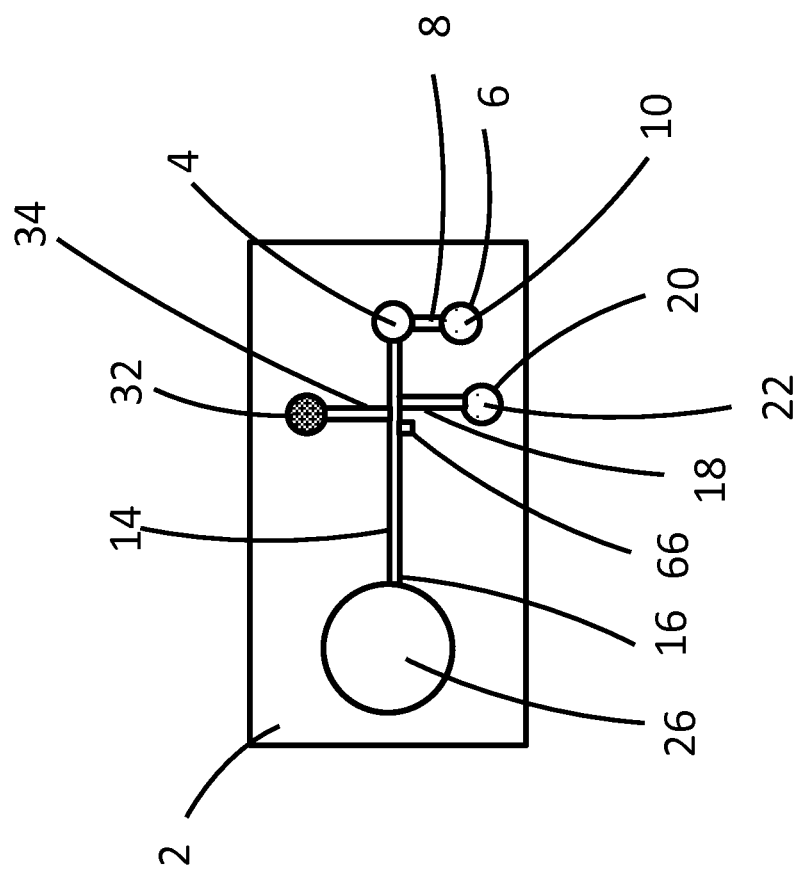

The device may be configured in any suitable arrangement, within the scope of the invention, for any or a particular application. FIGS. 5A-C teach three embodiments of the invention with different geometrical arrangements. FIG. 5A illustrates one embodiment in which the second overspill conduit 18 and the first fluid input conduit 34 are both perpendicular to the metering conduit 14, but on opposing sides of the metering conduit, and in which the first fluid input conduit 34 is offset slightly from the second overspill conduit 18. FIG. 5B illustrates another embodiment in which the second overspill conduit 18 is positioned at an angle to, but not perpendicular to, the metering conduit 14 in order to optimize the splitting of the second metered volume of fluid from the first metered volume of fluid. FIG. 5C illustrates yet a further embodiment in which a blind fluidic conduit 66 has been added to embodiment of FIG. 5A, which is positioned on the same side of the metering conduit 14 as the second overspill conduit 18 and laterally offset from the first fluid input conduit 34. In some examples, the blind fluidic conduit 66 helps the second metered volume of fluid to split from the first metered volume of fluid.

Figure 6A:
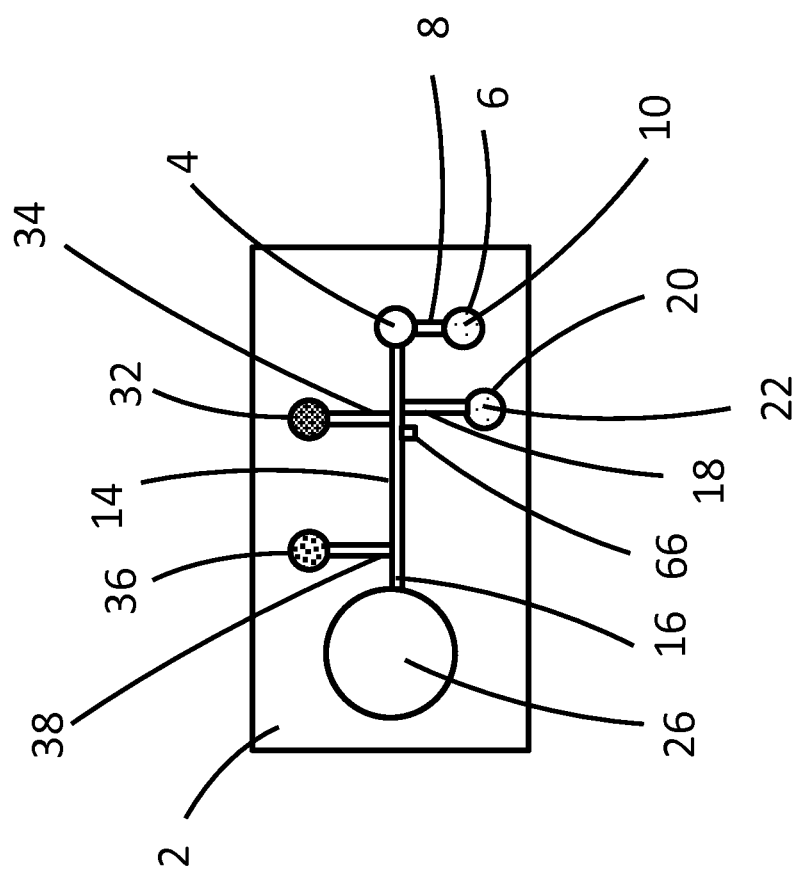
FIGS. 6A-D show three exemplary embodiments of fluidic chamber geometries within a housing with respect to the invention.
Figure 6B:
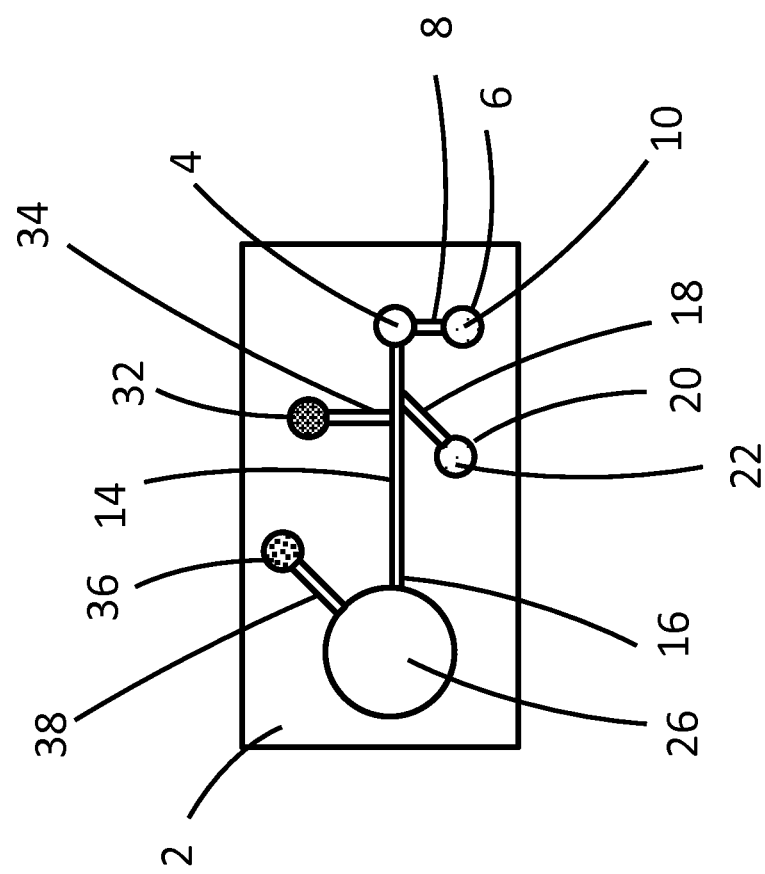
Figure 6C:
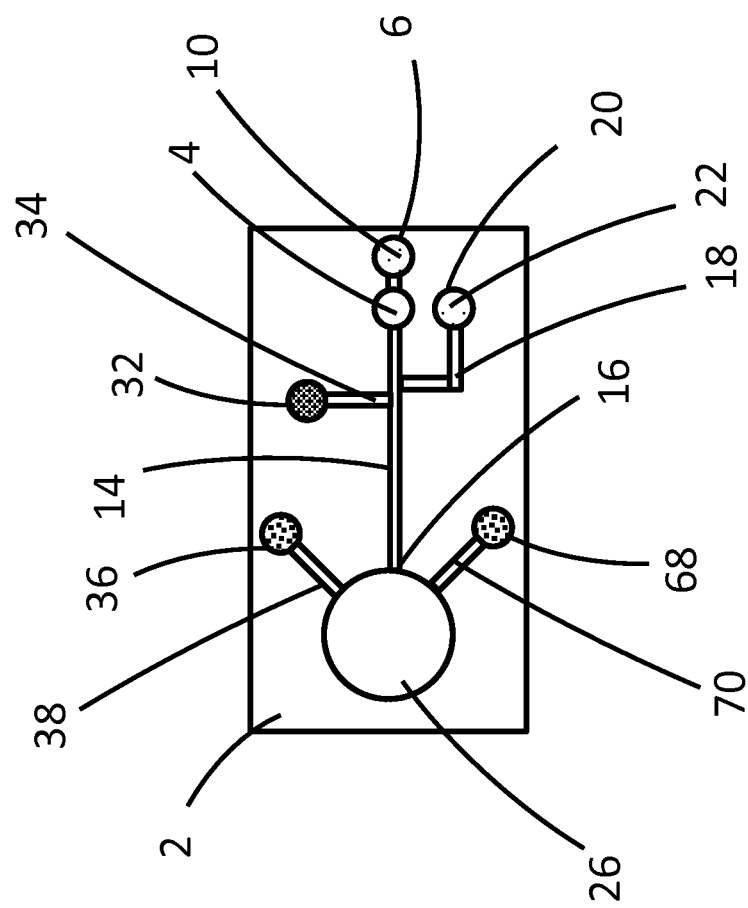
Figure 6D:
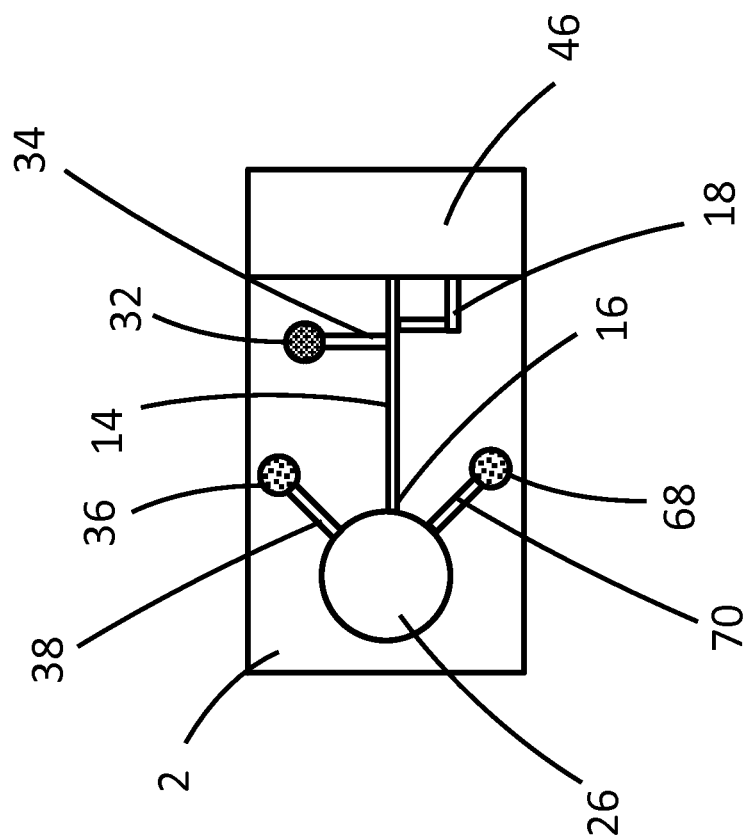

FIGS. 6A-C teach three different geometrical arrangements in which at least two additional fluids are input to the device. FIG. 6A teaches one embodiment in which a first fluid input conduit 34 and a second fluid input conduit 38 are both in communication with the metering conduit 14. In FIG. 6B, the first fluid input conduit 34 is in communication with the metering conduit 14 while the second fluid input conduit 38 is in communication with the mixing chamber 26. The embodiment of FIG. 6C has three fluid input conduits; the first fluid input conduit 34 is in communication with the metering conduit 14, while the second 38 and third 70 fluid input conduits are each separately in communication with the mixing chamber 26. As depicted in FIG. 6D, the closable lid 46 of the closes the device in FIG. 6C and seals the sample input chamber 4, the first vent 12 and the fluid actuated closable valve 22.

In exemplary embodiments, a sensor may be combined with and/or integrated into the microfluidic chip to monitor fluids in one or more fluidic conduits and/or one or more fluidic chambers. The sensor can be any sensor used for monitoring chemical, optical and/or electrical properties and/or constituents of a fluid, and may include, but not be limited to, impedance sensors, particle counters, lasers, LEDs, photodiodes, PMTs, pH sensors, EWOD, AM-EWOD or other suitable sensors.

Figure 7A:
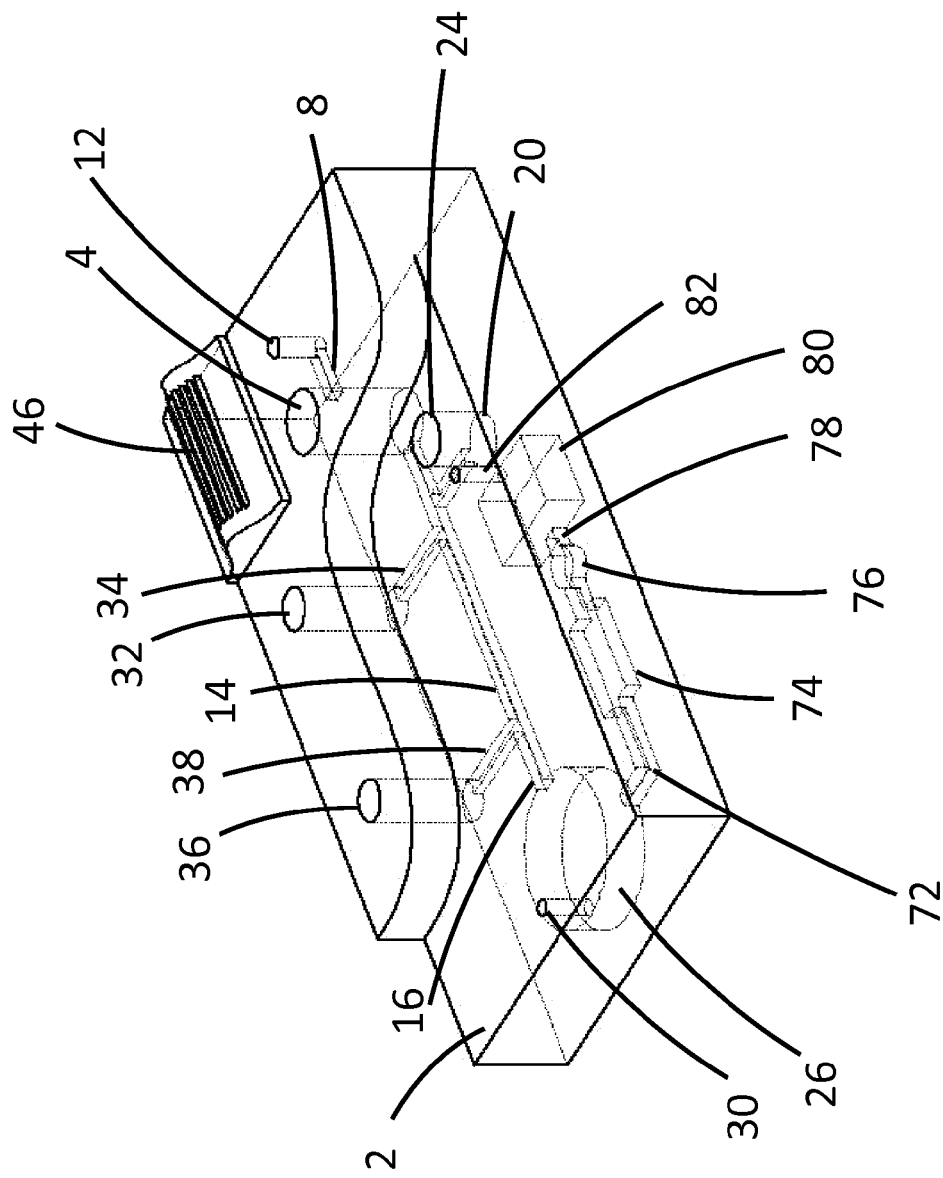
FIGS. 7A-B show an exemplary embodiment where sensors have been integrated into the housing with respect to the invention.
Figure 7B:
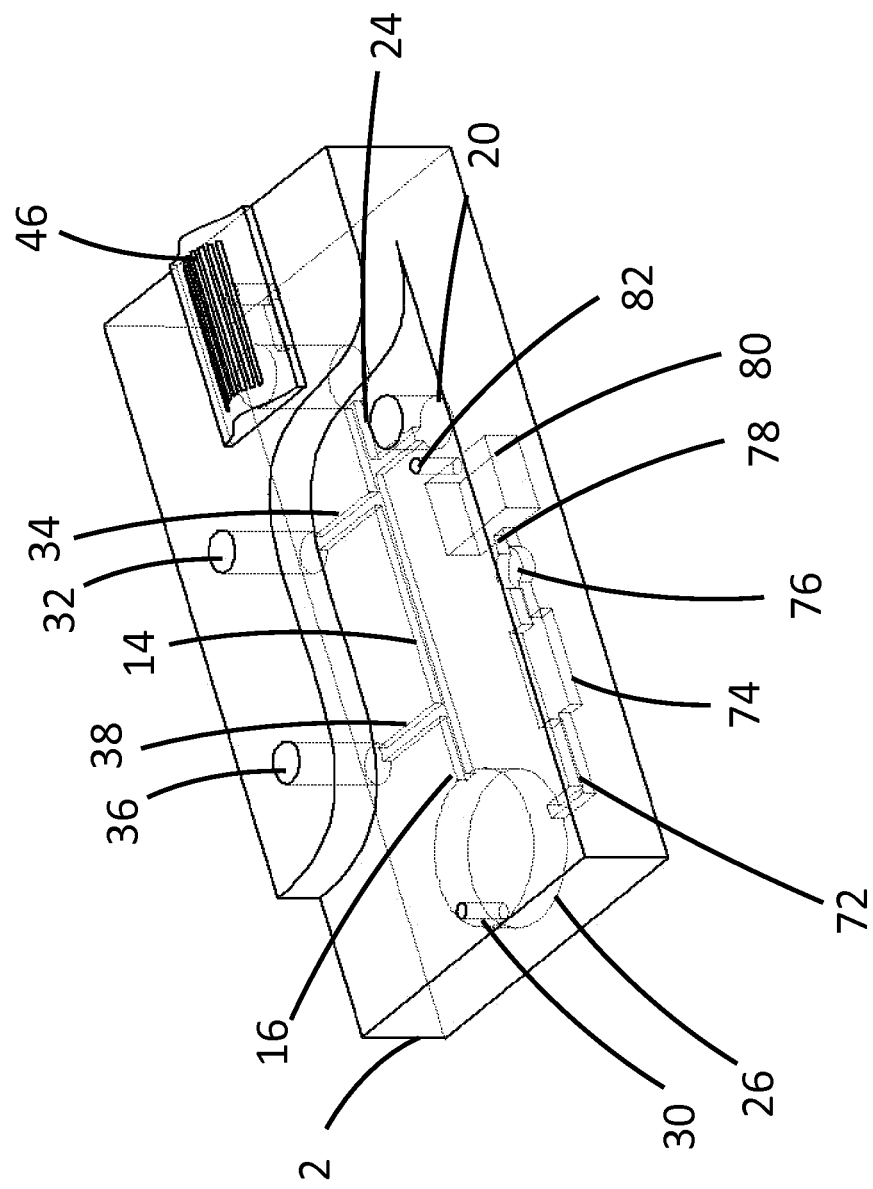

Referring to FIGS. 7A-B, In one embodiment of the invention, the base of the mixing chamber 26 is coupled to an output conduit 72 which is in communication with a microfluidic cell counter 74 for counting cells. In a further embodiment of the invention, the microfluidic cell counter 74 will be in communication with a hemoglobin measurement chamber 76, a waste conduit 78 and a waste chamber 80 containing a waste absorbent pad and a waste vent 82. FIGS. 7A-B teach one embodiment in which a microfluidic cell counter 74 is integrated into the fluidic device housing 2 with the closable lid 46 open (FIG. 7A), and closed (FIG. 7B).

A pressure displacement mechanism, omitted for clarity, may form the lid of the mixing chamber 26 which may then be utilised to control the flow of fluid from the mixing chamber 26, through the output conduit 72, through the microfluidic cell counter 74, through the hemoglobin measurement chamber 76 and into the waste chamber 80.

In one embodiment, the waste vent 82 is sealed until the fluid sample has been prepared in the mixing chamber 26. The waste vent 82 can then be pierced, or opened, before the prepared fluid is introduced to the microfluidic cell counter 74, hemoglobin measurement window 76 and waste chamber 80.

In a further embodiment of the invention, a validation check can be performed in order to confirm the exact volume of the second metered volume of fluid 44. This is advantageous for applications where knowing the exact volume of the second metered volume of fluid is critical, such as for example, in quantitative measurements. In one embodiment, optical measurements, such as for example fluorescence and/or absorption, may be made through the metering conduit. Given that the dimensions of the metering conduit are known, measuring the length of the second metered volume of fluid will enable the exact volume of the second metered volume of fluid to be confirmed and/or validated.

Figure 8A:
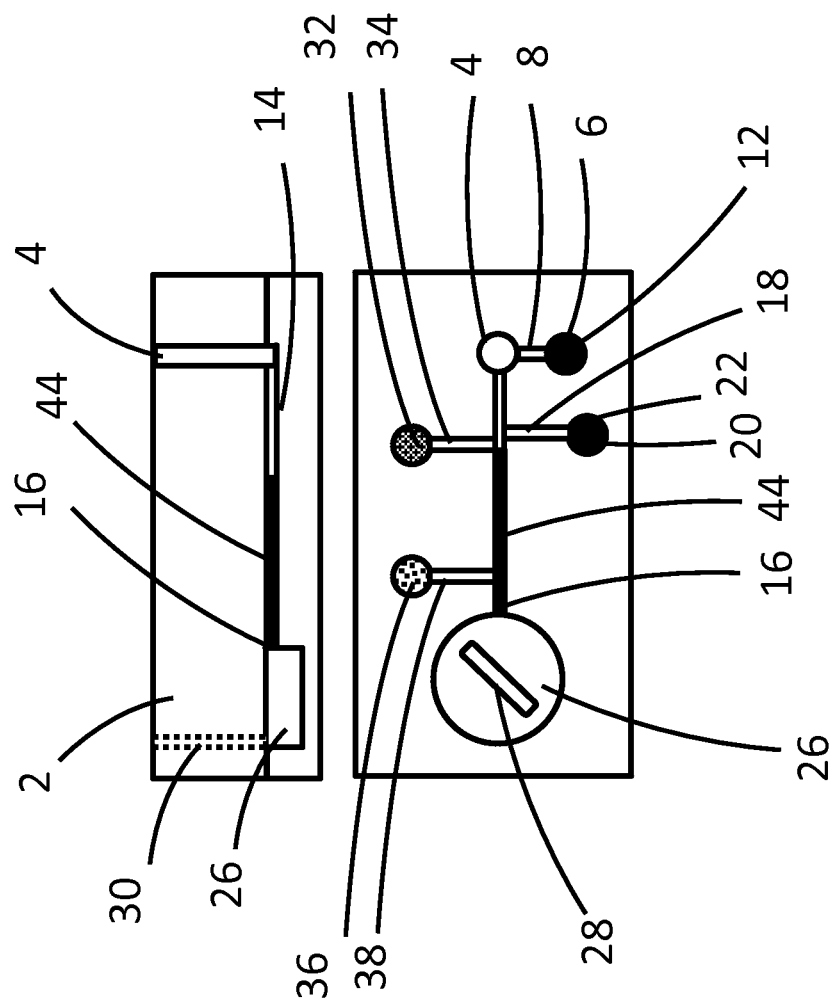
FIGS. 8A-B depict an example of how optical measurements may be made in the fluidic device according to an exemplary embodiment of the invention.
Figure 8B:
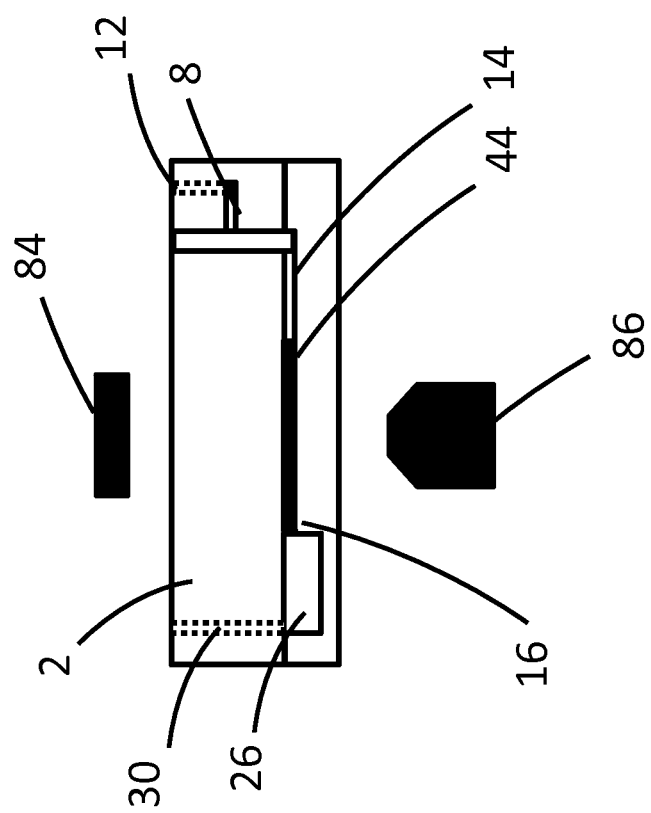

FIG. 8A illustrates one embodiment in which this validation technique can be performed. FIG. 8A presents a microfluidic device including a housing 2, a fluid input chamber 4, a first overspill conduit 8, a first overspill chamber 6, a first vent hole 12, a metering conduit 14, a capillary stop 16, a second overspill conduit 18, a fluid actuated closable valve 24, a first fluid input chamber 32, a first fluid input conduit 34, a second fluid input chamber 36, a second fluid input conduit 38, a mixing chamber 26 and a magnetic flea 28. After the first and second passive metering steps, a second metered volume of fluid 44 resides in the metering conduit 14 between the capillary stop 16 and the second overspill conduit 18. FIG. 8B shows one embodiment of how an optical sensing device, for example, photodiode 86 and photodetector 84 can be utilized to measure the length of the second metered volume of fluid 44 metered in the metering conduit 14 to validate the volume of the second metered volume of fluid. Alternatively, a camera may be used to determine the length of the second metered volume of fluid.

In accordance with the above, an aspect of the invention is a method of metering a fluid in an integrated fluidic device. In exemplary embodiments, the metering method may include the steps of: inputting a sample fluid from an input fluid sample chamber into a metering conduit; providing a first overspill chamber in fluid communication with the sample fluid input chamber and the metering conduit; passively metering a first metered volume of fluid with the metering conduit from the sample fluid, wherein the first overspill chamber receives fluid from the sample fluid in excess of the first metered volume of fluid; providing a second overspill chamber in fluid communication with the metering conduit; and passively metering a second metered volume of fluid with the metering conduit, wherein the second overspill chamber receives fluid from the first metered volume of fluid in excess of the second metered volume of fluid. The method further may include producing an air gap between the second metered volume of fluid in the metering conduit and the sample input chamber and second overspill conduit, thereby isolating the second metered volume of fluid from the sample fluid.

In view of such method, the invention may be further understood with reference to the following non-limiting examples.

Example 1

Lysing Red Blood Cells from a Whole Blood Sample 1 ul of whole human blood contains ~5 million red blood cells (RBCs), ~10,000 white blood cells (WBCs), and ~500,000 platelets. In order to accurately count the number of WBCs, the RBCs must be removed, e.g. lysed.

Any of the devices, for example, of FIGS. 2A-I, FIGS. 3A-I or FIGS. 6A-B is ideally suited for preparing for lysing a whole blood sample so that white blood cells (WBCs) may be counted. In one embodiment, the fluid input sample is whole blood, with the first fluidic chamber 32 containing a lysis solution and the second fluidic chamber 36 containing a quench solution. Lysis and quench fluidic operations are performed on the second metered volume of blood. The sample is then removed from the mixing chamber, via the second vent, and analysed using a suitable haematology cell counter. Alternatively, if an impedance sensor is integrated into the housing, as shown in FIG. 7A or 7B, then the sample may be analysed on chip.

Preferably, the blood that is input into the device will be exposed to an anti-coagulant agent, for example, EDTA salts, heparin or the like. In one embodiment, the sample input chamber and/or the metering conduit will have their surfaces pre-treated with such an anti-coagulation agent. Such compounds may be adhered to the surfaces of the conduit walls.

The lysis reagent is any reagent mixture containing a chemical known to lyse RBCs, such as for example, saponins or quarternary ammonium salts. Preferably, the lysis reagent used contains saponin. More preferably, the lysis reagent will be 0.12% v/v formic acid and 0.05% w/v saponin. The quench reagent is any reagent mixture known to halt or substantially reduce the rate of RBC lysis. Preferably, the quench reagent will be 0.6% w/v sodium carbonate and 3% w/v sodium chloride. Preferably, the blood:lysis reagents are mixed in a ratio of 1:12 and the blood:quench reagents are mixed in a ratio of 1:5.3.

Example 2

Blood Cell Labelling, Lysing and Quenching

The device of FIG. 6C, for example, is suited to labelling white blood cells in a whole blood sample with a fluorescent label and preparing the sample for analysis.

The input sample fluid is whole blood, with the first fluid input chamber 32 containing a pre-defined volume of a fluorescent label reagent, the second fluid input chamber 36 would contain a pre-defined volume of a lysis reagent, and the third fluid input chamber 68 would contain a pre-defined volume of a quench reagent.

Positive displacement pressure is used to displace the defined volume of fluorescent label reagent from the first fluid input chamber, through the first fluid input conduit, flush the second metered volume of blood out of the metering conduit and into the mixing chamber for incubation, which means providing an environment to facilitate the binding of the fluorescent label to the white blood cells. The magnetic flea would gently agitate the whole blood and fluorescent label reagent for incubation of a predetermined length of time. One role of the magnetic flea at this point is to help prevent sedimentation of the sample.

Positive displacement pressure is then used to displace the defined volume of lysis reagent from the second fluid input chamber, through the second fluid input conduit, and into the mixing chamber. The magnetic flea is then used to mix the defined volume of lysis reagent with the fluorescently labeled white blood cells in order to lyse and remove, the red blood cells.

Positive displacement pressure is then applied to displace the defined volume of quench solution from the third fluid input chamber, through the third fluid input conduit and into the mixing chamber. The magnetic flea is then used to mix the defined volume of quench reagent with the lysis reagent and the fluorescently labeled white blood cells in order to stop the lysing process to prevent any damage to the white blood cells.

The labeled and lysed blood sample can then be analysed using any suitable haematology cell counter with fluorescence monitoring capabilities.

Preferably, the blood that is input into the device will be exposed to an anti-coagulant agent, such as for example EDTA salts, heparin or the like. In one embodiment, the sample input chamber and/or the metering conduit will have their surfaces pre-treated with such an anti-coagulation agent. Such compounds may be adhered to the surfaces of the conduit walls.

The lysis reagent is any reagent mixture contains a chemical known to lyse RBCs, such as for example saponins or quarternary ammonium salts. Preferably, the lysis reagent used contains saponin. More preferably, the lysis reagent will be 0.12% v/v formic acid and 0.05% w/v saponin. The quench reagent is any reagent mixture known to halt or substantially reduce the rate of RBC lysis. Preferably, the quench reagent will be 0.6% w/v sodium carbonate and 3% w/v sodium chloride. Preferably, the blood:lysis reagents are mixed in a ratio of 1:12 and the blood:quench reagents are mixed in a ratio of 1:5.3.

Preferably, the fluorescent label is one designed to bind to a CD marker on the surface of a WBC. Is some embodiments, the fluorescent label reagent may include several different fluorescent labels that bind to different CD markers.

The sample can then be removed from the mixing chamber, e.g. via the second vent, and analysed using a suitable haematology cell counter.

Example 3

White Blood Cell and Hemoglobin Count

In addition to counting white blood cells, it is advantageous to be able to measure the amount of hemoglobin in a given blood sample. Hemoglobin is best measured after RBCs have been lysed.

The integrated device of FIG. 7A, for example, is suited to preparing a blood sample for WBC counting and hemoglobin measurement. In this example, the fluid input sample is whole blood, with the first fluidic chamber 32 containing a lysis solution and the second fluidic chamber 36 containing a quench solution. Lysis and quench fluidic operations are performed on a second metered volume of blood in the mixing chamber.

Positive displacement pressure is used to displace the defined volume of lysis reagent from the first fluid input chamber, through the first fluid input conduit, flush the second metered volume of blood out of the metering conduit and into the mixing chamber for incubation, which again means providing an environment lyse the red blood cells. The magnetic flea provides both shear and mixing forces to optimize lysing.

Positive displacement pressure is then be used to displace the defined volume of quench reagent from the second fluid input chamber, through the second fluid input conduit, the metering conduit and into the mixing chamber. The magnetic flea is then used to mix the defined volume of quench reagent with the lysed blood sample to stop the lysis process and prevent any lysis of the white blood cells.

The lysis reagent is any reagent mixture contains a chemical known to lyse RBCs, such as for example saponins or quarternary ammonium salts. Preferably, the lysis reagent used contains saponin. More preferably, the lysis reagent will be 0.12% v/v formic acid and 0.05% w/v saponin. The quench reagent is any reagent mixture known to halt or substantially reduce the rate of RBC lysis. Preferably, the quench reagent will be 0.6% w/v sodium carbonate and 3% w/v sodium chloride. Preferably, the blood:lysis reagents are mixed in a ratio of 1:12 and the blood:quench reagents are mixed in a ratio of 1:5.3. Preferably the second metered volume of fluid has a volume 0.1-20 ul, or a volume of 0.1-10 ul, and even more preferably 0.5-5 ul. In one embodiment, the second metered volume of fluid will have a volume of 5 ul, and thus meter 5 ul of whole blood. 60 ul of 0.12% v/v formic acid and 0.05% w/v saponin will preferably be pre-loaded into the first fluid input chamber, and 26.5 ul of 0.6% w/v sodium carbonate and 3% w/v sodium chloride will preferably be pre-loaded into the second fluid input chamber. After metering, lysing and quenching, a total volume of lysed and quenched blood will be 91.5 ul will be present in the mixing chamber.

The base of the mixing chamber is in communication with an output conduit which is in communication with a microfluidic cell counter. Positive displacement pressure is used to displace the lysed blood sample from the mixing chamber through the output conduit and through the microfluidic cell counter for white blood cell counting. Preferably, the microfluidic cell counter will be a microchannel impedance sensor with at least two pairs of electrodes for measuring a differential current as a blood cell passes between the two electrodes of the first electrode pair, then the two electrodes of the second electrode pair. Preferably, the microfluidic channel within the impedance sensor will have a cross-section that is 40 um×40 um square, with each electrode in the first and second electrode pairs also measuring 40 um×40 um square. Preferably, the fluid containing the blood cells to be counted will be pumped through the microchannel impedance sensor at a constant flow rate, most preferably at a flow rate of 40 ul/min.

The embodiment may further include a haemoglobin measurement in a haemoglobin measurement chamber. For haemoglobin to be measured accurately, the RBCs must be lysed. It is further preferable to convert the haemoglobin into a stable oxidized form (methemoglobin) by adding chemical haemoglobin reagent mixtures. Suitable reagents include, but are not limited to, Drabkins's reagent (which contains sodium bicarbonate, potassium ferricyanide and potassium cyanide and converts haemoglobin into cyanmethemoglobin), or ferrocyanide. Such haemoglobin reagents could be pre-dried in the haemoglobin measurement chamber. In practice, haemoglobin is converted to cyanmethemoglobin (e.g. by reacting the blood with a Drabkin's reagent) and measured spectrophotometrically (the reacted Drabkin's reagent and haemoglobin form a stable, coloured end-product). A simple LED/photodiode combination can be employed for the quantitative, colourimetric determination of blood haemoglobin using absorbance in accordance with Beer's law as is known in the art.

After cell counting, and the hemoglobin measurement, the processed blood samples are collected in a waste chamber where the waste is absorbed by an absorbent pad.

In accordance with the above description, an aspect of the invention is an integrated fluidic device. In exemplary embodiments, the integrated fluidic device includes a sample fluid input chamber that provides an input of a sample fluid, a first overspill chamber in fluid communication with the fluid input chamber, and a metering conduit in fluid communication with the fluid input chamber and the first overspill chamber. The metering conduit meters a first metered volume of fluid from the sample fluid, and the first overspill chamber receives fluid from the sample fluid in excess of the first metered volume of fluid. A second overspill chamber in fluid communication with the metering conduit. The metering conduit meters a second metered volume of fluid from the first metered volume of fluid, and the second overspill chamber receives fluid from the first metered volume of fluid in excess of the second metered volume of fluid.

In another exemplary embodiment of the integrated fluidic device, the second overspill chamber has a fluid actuated closable valve for controlling the metering of the second metered volume of fluid.

In another exemplary embodiment of the integrated fluidic device, the first overspill chamber includes a first absorbent pad for absorbing the fluid in excess of the first metered volume of fluid, and the fluid actuated closeable valve includes a second absorbent pad for absorbing the fluid in excess of the second metered volume of fluid.

In another exemplary embodiment of the integrated fluidic device, the first overspill chamber is in fluid communication with the metering conduit via a first overspill conduit, and the first overspill conduit is offset from the metering conduit.

In another exemplary embodiment of the integrated fluidic device, the device further includes a blind fluidic conduit to split the second metered volume of fluid from the first metered volume of fluid.

In another exemplary embodiment of the integrated fluidic device, the device further includes an optical sensor device that measures a length of the second metered volume of fluid to validate the volume of the second metered volume of fluid.

In another exemplary embodiment of the integrated fluidic device, the device further includes a capillary stop at an end of the metering conduit opposite the fluid input chamber, and a mixing chamber in fluid communication with the capillary stop, wherein the mixing chamber receives the second metered volume of fluid from the metering conduit through the capillary stop.

In another exemplary embodiment of the integrated fluidic device, the mixing chamber has a magnetic flea, and an aspect ratio of a length of the magnetic flea to a diameter of the mixing chamber is at least 0.5.

In another exemplary embodiment of the integrated fluidic device, the device further includes a closeable lid, and the first overspill chamber includes a vent hole, wherein the closeable lid closes over the vent hole to seal the sample fluid input chamber and force at least a portion of the second metered volume of fluid into the mixing chamber.

In another exemplary embodiment of the integrated fluidic device, the device further includes at least one further fluid input chamber in fluid communication with the metering conduit, wherein the mixing chamber receives a further fluid from the at least one further fluid input chamber through the metering conduit and the capillary stop.

In another exemplary embodiment of the integrated fluidic device, the at least one further fluid chamber includes a pressure displacement mechanism for transferring the further fluid from the at least one further fluid chamber into the metering conduit.

In another exemplary embodiment of the integrated fluidic device, the at least one further fluid chamber has first and second frangible seals, and the pressure displacement mechanism is a moveable piston. The moveable piston has a needle that pierces the first and second frangible seals to transfer the further fluid from the at least one further fluid chamber into the metering conduit.

In another exemplary embodiment of the integrated fluidic device, the integrated fluidic device has n further fluid input chambers, where n is greater than or equal to two.

In another exemplary embodiment of the integrated fluidic device, the device further includes an output conduit in fluid communication with the mixing chamber, and a cell counter in fluid communication with the output conduit. Fluid is transferred to the cell counter from the mixing chamber via the output conduit, and the center counter counts cells that are present in the fluid transferred from the mixing chamber.

In another exemplary embodiment of the integrated fluidic device, the cell counter has at least one of a white blood cell counter or a hemoglobin measurement chamber.

Another aspect of the invention is a method of metering a fluid in an integrated fluidic device. Exemplary embodiments of the method of metering a fluid include the steps of: inputting a sample fluid from an input fluid sample chamber into a metering conduit; providing a first overspill chamber in fluid communication with the sample fluid input chamber and the metering conduit; passively metering a first metered volume of fluid with the metering conduit from the sample fluid, wherein the first overspill chamber receives fluid from the sample fluid in excess of the first metered volume of fluid; providing a second overspill chamber in fluid communication with the metering conduit; and passively metering a second metered volume of fluid with the metering conduit, wherein the second overspill chamber receives fluid from the first metered volume of fluid in excess of the second metered volume of fluid.

In another embodiment of the method of metering a fluid, the method further includes producing an air gap between the second metered volume of fluid in the metering conduit and the sample input chamber and second overspill conduit, thereby isolating the second metered volume of fluid from the sample fluid.

In another embodiment of the method of metering a fluid, the method further includes transferring the second metered volume of fluid into a mixing chamber, and performing at least one fluidic operation in the mixing chamber.

In another embodiment of the method of metering a fluid, the method further includes providing at least one further fluid input chamber in fluid communication with the metering conduit, and transferring a further fluid from the at least one further fluid input chamber through the metering conduit and into the mixing chamber.

In another embodiment of the method of metering a fluid, the method further includes outputting fluid from the mixing chamber, and transferring the outputted fluid to a cell counter, the center counter counts cells that are present in the fluid transferred from the mixing chamber.

While the invention has been described with respect to certain embodiments, equivalent modifications and alterations may occur to one skilled in the art, within the spirit and scope of the appended claims, upon the reading and understanding of the specification and the annexed drawings. In addition, while a particular feature of the invention may have been described with respect to only one or more of several embodiments, such features may be combined with one or more other features of different embodiments as may be desired and advantageous for any given or particular application.

INDUSTRIAL APPLICABILITY

The microfluidic device could form a part of a lab-on-a-chip system. Such devices could be used in metering, mixing, reacting, lysing, quenching, binding, labeling and/or sensing chemical, biochemical, physiological, and/or environmental fluids.

The microfluidic device could further form part of a point-of-care diagnostic testing system for cell counting, e.g. WBC count and analysis.

What is claimed is:

1. An integrated fluidic device comprising:
    a sample fluid input chamber configured to provide an input of a sample fluid;
    a first overspill chamber in fluid communication with the fluid input chamber;
    a metering conduit in fluid communication with the fluid input chamber and the first overspill chamber, wherein the metering conduit is configured to meter a first metered volume of fluid from the sample fluid, and the first overspill chamber is configured to receive fluid from the sample fluid in excess of the first metered volume of fluid; and
    a second overspill chamber in fluid communication with the metering conduit, wherein the metering conduit is configured to meter a second metered volume of fluid from the first metered volume of fluid, and the second overspill chamber is configured to receive fluid from the first metered volume of fluid in excess of the second metered volume of fluid;
    wherein the second overspill chamber has a fluid actuated closable valve configured to isolate the second metered volume of fluid out of the first metered volume of fluid when the fluid actuated closable valve closes; and
    wherein the first overspill chamber includes a first absorbent pad configured to absorb the fluid in excess of the first metered volume of fluid, and the fluid actuated closeable valve includes a second absorbent pad configured to absorb the fluid in excess of the second metered volume of fluid.

2. The integrated fluidic device of claim 1, wherein the first overspill chamber is in fluid communication with the metering conduit via a first overspill conduit, and the first overspill conduit is offset from the metering conduit.

3. The integrated fluidic device of claim 1, further comprising a blind fluidic conduit configured to split the second metered volume of fluid from the first metered volume of fluid.

4. The integrated fluidic device of claim 1, further comprising an optical sensor device that measures a length of the second metered volume of fluid to validate the volume of the second metered volume of fluid.

5. The integrated fluidic device of claim 1, further comprising:
    a capillary stop at an end of the metering conduit opposite the fluid input chamber; and
    a mixing chamber in fluid communication with the capillary stop, wherein the mixing chamber is configured to receive the second metered volume of fluid from the metering conduit through the capillary stop.

6. The integrated fluidic device of claim 5, wherein the mixing chamber has a magnetic flea, and an aspect ratio of a length of the magnetic flea to a diameter of the mixing chamber is at least 0.5.

7. The integrated fluidic device of claim 5, further comprising a closeable lid, and the first overspill chamber includes a vent hole, wherein the closeable lid is configured to close over the vent hole to seal the sample fluid input chamber and force at least a portion of the second metered volume of fluid into the mixing chamber.

8. The integrated fluidic device of claim 5, further comprising at least one further fluid input chamber in fluid communication with the metering conduit, wherein the mixing chamber is configured to receive a further fluid from the at least one further fluid input chamber through the metering conduit and the capillary stop.

9. The integrated fluidic device of claim 8, wherein the at least one further fluid chamber includes a pressure displacement mechanism configured to transfer the further fluid from the at least one further fluid chamber into the metering conduit.

10. The integrated fluidic device of claim 9, wherein the at least one further fluid chamber has first and second frangible seals, and the pressure displacement mechanism is a moveable piston; and wherein the moveable piston has a needle that is configured to pierce the first and second frangible seals to transfer the further fluid from the at least one further fluid chamber into the metering conduit.

11. The integrated fluidic device of claim 8, wherein the integrated fluidic device has n further fluid input chambers, where n is greater than or equal to two.

12. The integrated fluidic device of claim 1, further comprising:

an output conduit in fluid communication with the mixing chamber; and a cell counter in fluid communication with the output conduit;

wherein the output conduit is configured to transfer fluid to the cell counter from the mixing chamber, and the cell counter is configured to count cells that are present in the fluid transferred from the mixing chamber.

13. The integrated fluidic device of claim 12, further wherein the cell counter comprises at least one of a white blood cell counter or a hemoglobin measurement chamber.

* * * * *